United States Patent
Levy et al.

(10) Patent No.: US 9,688,991 B2
(45) Date of Patent: Jun. 27, 2017

(54) APTAMER-TARGETTED ANTIGEN DELIVERY

(71) Applicant: ALBERT EINSTEIN COLLEGE OF MEDICINE OF YESHIVA UNIVERSITY, Bronx, NY (US)

(72) Inventors: Matthew Levy, New Rochelle, NY (US); Deborah Palliser, Bronx, NY (US); Brian Christopher Wengerter, Bronx, NY (US); Steven Craig Almo, Pelham, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 0 days.

(21) Appl. No.: 14/413,727

(22) PCT Filed: Jul. 3, 2013

(86) PCT No.: PCT/US2013/049212
§ 371 (c)(1),
(2) Date: Jan. 9, 2015

(87) PCT Pub. No.: WO2014/011465
PCT Pub. Date: Jan. 16, 2014

(65) Prior Publication Data
US 2015/0191730 A1    Jul. 9, 2015

Related U.S. Application Data

(60) Provisional application No. 61/671,239, filed on Jul. 13, 2012.

(51) Int. Cl.
| | |
|---|---|
| *C12N 15/115* | (2010.01) |
| *A61K 39/385* | (2006.01) |
| *A61K 47/48* | (2006.01) |
| A61K 39/00 | (2006.01) |
| C12N 15/113 | (2010.01) |

(52) U.S. Cl.
CPC .......... *C12N 15/115* (2013.01); *A61K 39/385* (2013.01); *A61K 47/48092* (2013.01); *A61K 2039/6025* (2013.01); *C12N 15/1138* (2013.01); *C12N 2310/14* (2013.01); *C12N 2310/16* (2013.01); *C12N 2310/3513* (2013.01); *C12N 2320/32* (2013.01)

(58) Field of Classification Search
CPC .............. C12N 15/115; C12N 2310/16; A61K 39/385; A61K 47/4809; A61K 2039/6025
See application file for complete search history.

(56) References Cited

U.S. PATENT DOCUMENTS

| | | |
|---|---|---|
| 2004/0031072 A1 | 2/2004 | La Rosa et al. |
| 2013/0123478 A1 | 5/2013 | Levy et al. |

FOREIGN PATENT DOCUMENTS

| | | |
|---|---|---|
| WO | 9960169 A1 | 11/1999 |
| WO | 2012012518 A2 | 1/2012 |
| WO | 2013163303 A2 | 10/2013 |
| WO | 2014011465 A2 | 1/2014 |
| WO | 2015066001 A1 | 5/2015 |

OTHER PUBLICATIONS

PCT International Search Report and Written Opinion, dated Dec. 20, 2013 in connection with PCT International Application No. PCT/US2013/49212 11 pages.

*Primary Examiner* — Jon E Angell
(74) *Attorney, Agent, or Firm* — Amster, Rothstein & Ebenstein LLP

(57) ABSTRACT

A composition is provided comprising an oligonucleotide aptamer conjugated to an antigen, wherein the aptamer is directed against a cell-surface target of an antigen-presenting cell. Also provided are methods of delivering an antigen to a dendritic cell and of eliciting an immune response in a subject.

13 Claims, 9 Drawing Sheets

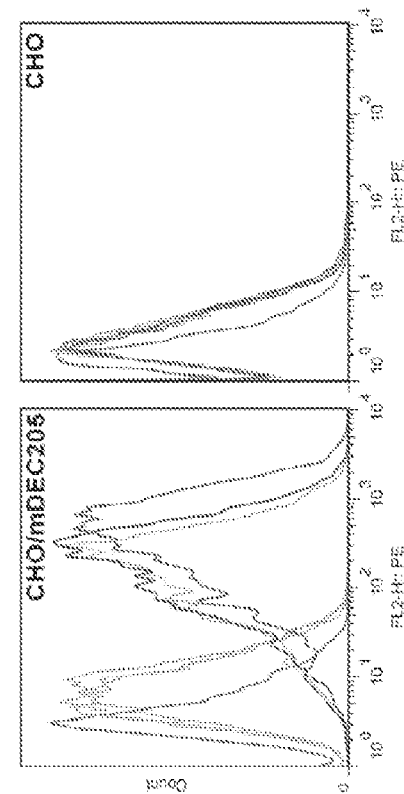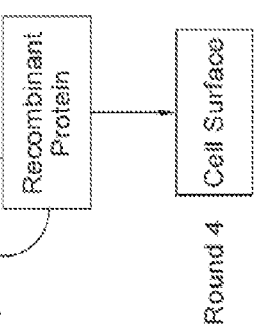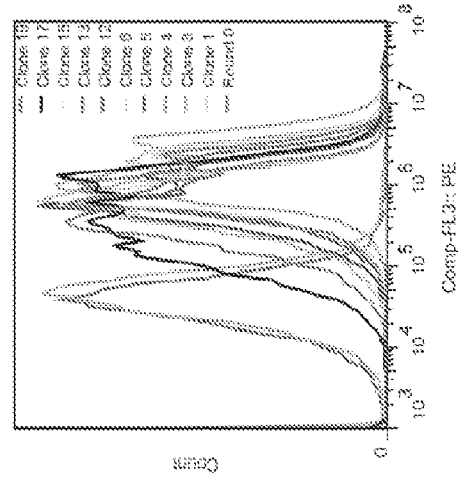
Fig. 1A-1D

SEQUENCE LISTING

```
<160> NUMBER OF SEQ ID NOS: 12

<210> SEQ ID NO 1
<211> LENGTH: 42
<212> TYPE: RNA
<213> ORGANISM: Artificial Sequence
<220> FEATURE:
<223> OTHER INFORMATION: ARTIFICIAL APTAMER SEQUENCE DIRECTED TO DEC-205

<400> SEQUENCE: 1
gggaggugug uuagcacacg auucauaauc agcuacccuc cc                             42

<210> SEQ ID NO 2
<211> LENGTH: 1722
<212> TYPE: PRT
<213> ORGANISM: HOMO SAPIENS

<400> SEQUENCE: 2

Met Arg Thr Gly Trp Ala Thr Pro Arg Arg Pro Ala Gly Leu Leu Met
1               5                   10                  15

Leu Leu Phe Trp Phe Phe Asp Leu Ala Glu Pro Ser Gly Arg Ala Ala
                20                  25                  30

Asn Asp Pro Phe Thr Ile Val His Gly Asn Thr Gly Lys Cys Ile Lys
            35                  40                  45

Pro Val Tyr Gly Trp Ile Val Ala Asp Asp Cys Asp Glu Thr Glu Asp
        50                  55                  60

Lys Leu Trp Lys Trp Val Ser Gln His Arg Leu Phe His Leu His Ser
65                  70                  75                  80

Gln Lys Cys Leu Gly Leu Asp Ile Thr Lys Ser Val Asn Glu Leu Arg
                85                  90                  95

Met Phe Ser Cys Asp Ser Ser Ala Met Leu Trp Trp Lys Cys Glu His
            100                 105                 110

His Ser Leu Tyr Gly Ala Ala Arg Tyr Arg Leu Ala Leu Lys Asp Gly
        115                 120                 125

His Gly Thr Ala Ile Ser Asn Ala Ser Asp Val Trp Lys Lys Gly Gly
    130                 135                 140

Ser Glu Glu Ser Leu Cys Asp Gln Pro Tyr His Glu Ile Tyr Thr Arg
145                 150                 155                 160
```

-continued

```
Asp Gly Asn Ser Tyr Gly Arg Pro Cys Glu Phe Pro Phe Leu Ile Asp
            165                 170                 175
Gly Thr Trp His His Asp Cys Ile Leu Asp Glu Asp His Ser Gly Pro
        180                 185                 190
Trp Cys Ala Thr Thr Leu Asn Tyr Glu Tyr Asp Arg Lys Trp Gly Ile
        195                 200                 205
Cys Leu Lys Pro Glu Asn Gly Cys Glu Asp Asn Trp Glu Lys Asn Glu
    210                 215                 220
Gln Phe Gly Ser Cys Tyr Gln Phe Asn Thr Gln Thr Ala Leu Ser Trp
225                 230                 235                 240
Lys Glu Ala Tyr Val Ser Cys Gln Asn Gln Gly Ala Asp Leu Leu Ser
            245                 250                 255
Ile Asn Ser Ala Ala Glu Leu Thr Tyr Leu Lys Glu Lys Glu Gly Ile
        260                 265                 270
Ala Lys Ile Phe Trp Ile Gly Leu Asn Gln Leu Tyr Ser Ala Arg Gly
        275                 280                 285
Trp Glu Trp Ser Asp His Lys Pro Leu Asn Phe Leu Asn Trp Asp Pro
    290                 295                 300
Asp Arg Pro Ser Ala Pro Thr Ile Gly Gly Ser Ser Cys Ala Arg Met
305                 310                 315                 320
Asp Ala Glu Ser Gly Leu Trp Gln Ser Phe Ser Cys Glu Ala Gln Leu
            325                 330                 335
Pro Tyr Val Cys Arg Lys Pro Leu Asn Asn Thr Val Glu Leu Thr Asp
        340                 345                 350
Val Trp Thr Tyr Ser Asp Thr Arg Cys Asp Ala Gly Trp Leu Pro Asn
        355                 360                 365
Asn Gly Phe Cys Tyr Leu Leu Val Asn Glu Ser Asn Ser Trp Asp Lys
    370                 375                 380
Ala His Ala Lys Cys Lys Ala Phe Ser Ser Asp Leu Ile Ser Ile His
385                 390                 395                 400
Ser Leu Ala Asp Val Glu Val Val Thr Lys Leu His Asn Glu Asp
            405                 410                 415
Ile Lys Glu Glu Val Trp Ile Gly Leu Lys Asn Ile Asn Ile Pro Thr
        420                 425                 430
Leu Phe Gln Trp Ser Asp Gly Thr Glu Val Thr Leu Thr Tyr Trp Asp
    435                 440                 445
Glu Asn Glu Pro Asn Val Pro Tyr Asn Lys Thr Pro Asn Cys Val Ser
    450                 455                 460
Tyr Leu Gly Glu Leu Gly Gln Trp Lys Val Gln Ser Cys Glu Glu Lys
465                 470                 475                 480
Leu Lys Tyr Val Cys Lys Arg Lys Gly Glu Lys Leu Asn Asp Ala Ser
            485                 490                 495
Ser Asp Lys Met Cys Pro Pro Asp Glu Gly Trp Lys Arg His Gly Glu
        500                 505                 510
Thr Cys Tyr Lys Ile Tyr Glu Asp Glu Val Pro Phe Gly Thr Asn Cys
        515                 520                 525
Asn Leu Thr Ile Thr Ser Arg Phe Glu Gln Glu Tyr Leu Asn Asp Leu
    530                 535                 540
Met Lys Lys Tyr Asp Lys Ser Leu Arg Lys Tyr Phe Trp Thr Gly Leu
545                 550                 555                 560
Arg Asp Val Asp Ser Cys Gly Glu Tyr Asn Trp Ala Thr Val Gly Gly
            565                 570                 575
Arg Arg Arg Ala Val Thr Phe Ser Asn Trp Asn Phe Leu Glu Pro Ala
```

-continued

```
                580                 585                 590
Ser Pro Gly Gly Cys Val Ala Met Ser Thr Gly Lys Ser Val Gly Lys
                595                 600                 605
Trp Glu Val Lys Asp Cys Arg Ser Phe Lys Ala Leu Ser Ile Cys Lys
        610                 615                 620
Lys Met Ser Gly Pro Leu Gly Pro Glu Ala Ser Pro Lys Pro Asp
625                 630                 635                 640
Asp Pro Cys Pro Glu Gly Trp Gln Ser Phe Pro Ala Ser Leu Ser Cys
                645                 650                 655
Tyr Lys Val Phe His Ala Glu Arg Ile Val Arg Lys Arg Asn Trp Glu
                660                 665                 670
Glu Ala Glu Arg Phe Cys Gln Ala Leu Gly Ala His Leu Ser Ser Phe
        675                 680                 685
Ser His Val Asp Glu Ile Lys Glu Phe Leu His Phe Leu Thr Asp Gln
        690                 695                 700
Phe Ser Gly Gln His Trp Leu Trp Ile Gly Leu Asn Lys Arg Ser Pro
705                 710                 715                 720
Asp Leu Gln Gly Ser Trp Gln Trp Ser Asp Arg Thr Pro Val Ser Thr
                725                 730                 735
Ile Ile Met Pro Asn Glu Phe Gln Gln Asp Tyr Asp Ile Arg Asp Cys
                740                 745                 750
Ala Ala Val Lys Val Phe His Arg Pro Trp Arg Arg Gly Trp His Phe
                755                 760                 765
Tyr Asp Asp Arg Glu Phe Ile Tyr Leu Arg Pro Phe Ala Cys Asp Thr
        770                 775                 780
Lys Leu Glu Trp Val Cys Gln Ile Pro Lys Gly Arg Thr Pro Lys Thr
785                 790                 795                 800
Pro Asp Trp Tyr Asn Pro Asp Arg Ala Gly Ile His Gly Pro Pro Leu
                805                 810                 815
Ile Ile Glu Gly Ser Glu Tyr Trp Phe Val Ala Asp Leu His Leu Asn
                820                 825                 830
Tyr Glu Glu Ala Val Leu Tyr Cys Ala Ser Asn His Ser Phe Leu Ala
                835                 840                 845
Thr Ile Thr Ser Phe Val Gly Leu Lys Ala Ile Lys Asn Lys Ile Ala
        850                 855                 860
Asn Ile Ser Gly Asp Gly Gln Lys Trp Trp Ile Arg Ile Ser Glu Trp
865                 870                 875                 880
Pro Ile Asp Asp His Phe Thr Tyr Ser Arg Tyr Pro Trp His Arg Phe
                885                 890                 895
Pro Val Thr Phe Gly Glu Glu Cys Leu Tyr Met Ser Ala Lys Thr Trp
                900                 905                 910
Leu Ile Asp Leu Gly Lys Pro Thr Asp Cys Ser Thr Lys Leu Pro Phe
        915                 920                 925
Ile Cys Glu Lys Tyr Asn Val Ser Ser Leu Lys Tyr Ser Pro Asp
        930                 935                 940
Ser Ala Ala Lys Val Gln Cys Ser Glu Gln Trp Ile Pro Phe Gln Asn
945                 950                 955                 960
Lys Cys Phe Leu Lys Ile Lys Pro Val Ser Leu Thr Phe Ser Gln Ala
                965                 970                 975
Ser Asp Thr Cys His Ser Tyr Gly Gly Thr Leu Pro Ser Val Leu Ser
                980                 985                 990
Gln Ile Glu Gln Asp Phe Ile Thr Ser Leu Leu Pro Asp Met Glu Ala
        995                 1000                1005
```

-continued

Thr Leu Trp Ile Gly Leu Arg Trp Thr Ala Tyr Glu Lys Ile Asn
1010                1015                1020

Lys Trp Thr Asp Asn Arg Glu Leu Thr Tyr Ser Asn Phe His Pro
1025                1030                1035

Leu Leu Val Ser Gly Arg Leu Arg Ile Pro Glu Asn Phe Phe Glu
1040                1045                1050

Glu Ser Arg Tyr His Cys Ala Leu Ile Leu Asn Leu Gln Lys
1055                1060                1065

Ser Pro Phe Thr Gly Thr Trp Asn Phe Thr Ser Cys Ser Glu Arg
1070                1075                1080

His Phe Val Ser Leu Cys Gln Lys Tyr Ser Glu Val Lys Ser Arg
1085                1090                1095

Gln Thr Leu Gln Asn Ala Ser Glu Thr Val Lys Tyr Leu Asn Asn
1100                1105                1110

Leu Tyr Lys Ile Ile Pro Lys Thr Leu Thr Trp His Ser Ala Lys
1115                1120                1125

Arg Glu Cys Leu Lys Ser Asn Met Gln Leu Val Ser Ile Thr Asp
1130                1135                1140

Pro Tyr Gln Gln Ala Phe Leu Ser Val Gln Ala Leu Leu His Asn
1145                1150                1155

Ser Ser Leu Trp Ile Gly Leu Phe Ser Gln Asp Glu Leu Asn
1160                1165                1170

Phe Gly Trp Ser Asp Gly Lys Arg Leu His Phe Ser Arg Trp Ala
1175                1180                1185

Glu Thr Asn Gly Gln Leu Glu Asp Cys Val Val Leu Asp Thr Asp
1190                1195                1200

Gly Phe Trp Lys Thr Val Asp Cys Asn Asp Asn Gln Pro Gly Ala
1205                1210                1215

Ile Cys Tyr Tyr Ser Gly Asn Glu Thr Glu Lys Glu Val Lys Pro
1220                1225                1230

Val Asp Ser Val Lys Cys Pro Ser Pro Val Leu Asn Thr Pro Trp
1235                1240                1245

Ile Pro Phe Gln Asn Cys Cys Tyr Asn Phe Ile Ile Thr Lys Asn
1250                1255                1260

Arg His Met Ala Thr Thr Gln Asp Glu Val His Thr Lys Cys Gln
1265                1270                1275

Lys Leu Asn Pro Lys Ser His Ile Leu Ser Ile Arg Asp Glu Lys
1280                1285                1290

Glu Asn Asn Phe Val Leu Glu Gln Leu Leu Tyr Phe Asn Tyr Met
1295                1300                1305

Ala Ser Trp Val Met Leu Gly Ile Thr Tyr Arg Asn Asn Ser Leu
1310                1315                1320

Met Trp Phe Asp Lys Thr Pro Leu Ser Tyr Thr His Trp Arg Ala
1325                1330                1335

Gly Arg Pro Thr Ile Lys Asn Glu Lys Phe Leu Ala Gly Leu Ser
1340                1345                1350

Thr Asp Gly Phe Trp Asp Ile Gln Thr Phe Lys Val Ile Glu Glu
1355                1360                1365

Ala Val Tyr Phe His Gln His Ser Ile Leu Ala Cys Lys Ile Glu
1370                1375                1380

Met Val Asp Tyr Lys Glu Glu His Asn Thr Thr Leu Pro Gln Phe
1385                1390                1395

```
Met Pro Tyr Glu Asp Gly Ile Tyr Ser Val Ile Gln Lys Lys Val
    1400                1405                1410

Thr Trp Tyr Glu Ala Leu Asn Met Cys Ser Gln Ser Gly Gly His
    1415                1420                1425

Leu Ala Ser Val His Asn Gln Asn Gly Gln Leu Phe Leu Glu Asp
    1430                1435                1440

Ile Val Lys Arg Asp Gly Phe Pro Leu Trp Val Gly Leu Ser Ser
    1445                1450                1455

His Asp Gly Ser Glu Ser Ser Phe Glu Trp Ser Asp Gly Ser Thr
    1460                1465                1470

Phe Asp Tyr Ile Pro Trp Lys Gly Gln Thr Ser Pro Gly Asn Cys
    1475                1480                1485

Val Leu Leu Asp Pro Lys Gly Thr Trp Lys His Glu Lys Cys Asn
    1490                1495                1500

Ser Val Lys Asp Gly Ala Ile Cys Tyr Lys Pro Thr Lys Ser Lys
    1505                1510                1515

Lys Leu Ser Arg Leu Thr Tyr Ser Ser Arg Cys Pro Ala Ala Lys
    1520                1525                1530

Glu Asn Gly Ser Arg Trp Ile Gln Tyr Lys Gly His Cys Tyr Lys
    1535                1540                1545

Ser Asp Gln Ala Leu His Ser Phe Ser Glu Ala Lys Lys Leu Cys
    1550                1555                1560

Ser Lys His Asp His Ser Ala Thr Ile Val Ser Ile Lys Asp Glu
    1565                1570                1575

Asp Glu Asn Lys Phe Val Ser Arg Leu Met Arg Glu Asn Asn Asn
    1580                1585                1590

Ile Thr Met Arg Val Trp Leu Gly Leu Ser Gln His Ser Val Asp
    1595                1600                1605

Gln Ser Trp Ser Trp Leu Asp Gly Ser Glu Val Thr Phe Val Lys
    1610                1615                1620

Trp Glu Asn Lys Ser Lys Ser Gly Val Gly Arg Cys Ser Met Leu
    1625                1630                1635

Ile Ala Ser Asn Glu Thr Trp Lys Lys Val Glu Cys Glu His Gly
    1640                1645                1650

Phe Gly Arg Val Val Cys Lys Val Pro Leu Gly Pro Asp Tyr Thr
    1655                1660                1665

Ala Ile Ala Ile Ile Val Ala Thr Leu Ser Ile Leu Val Leu Met
    1670                1675                1680

Gly Gly Leu Ile Trp Phe Leu Phe Gln Arg His Arg Leu His Leu
    1685                1690                1695

Ala Gly Phe Ser Ser Val Arg Tyr Ala Gln Gly Val Asn Glu Asp
    1700                1705                1710

Glu Ile Met Leu Pro Ser Phe His Asp
    1715                1720

<210> SEQ ID NO 3
<211> LENGTH: 7
<212> TYPE: RNA
<213> ORGANISM: Artificial Sequence
<220> FEATURE:
<223> OTHER INFORMATION: SEQUENCE COMMON TO ARTIFICIAL APTAMERS

<400> SEQUENCE: 3 uucauaa                                                                      7
```

-continued

```
<210> SEQ ID NO 4
<211> LENGTH: 72
<212> TYPE: DNA
<213> ORGANISM: Artificial Sequence
<220> FEATURE:
<223> OTHER INFORMATION: ARTIFICIALLY GENERATED CLONE LIBRARY
<220> FEATURE:
<221> NAME/KEY: misc_feature
<222> LOCATION: (23)..(23)
<223> OTHER INFORMATION: N = FROM 1 TO 50 NUCLEOTIDES, EACH OF WHICH MAY
      BE, INDEPENDENTLY, AN A, T, C OR G

<400> SEQUENCE: 4
gggaggtgaa tggttctacg atnttacatg cgagatgacc acgtaattga attaaatgcc      60
cgccatgacc ag                                                          72

<210> SEQ ID NO 5
<211> LENGTH: 38
<212> TYPE: DNA
<213> ORGANISM: Artificial Sequence
<220> FEATURE:
<223> OTHER INFORMATION: ARTIFICIAL APTAMER
<220> FEATURE:
<221> NAME/KEY: misc_feature
<222> LOCATION: (38)..(38)
<223> OTHER INFORMATION: T = INVERTED THYMIDINE

<400> SEQUENCE: 5
sggcguagug auuaugaauc gugugcuaau acacgcct                              38

<210> SEQ ID NO 6
<211> LENGTH: 25
<212> TYPE: DNA
<213> ORGANISM: Artificial Sequence
<220> FEATURE:
<223> OTHER INFORMATION: SIRNA DIRECTED AGAINST MOUSE DEC205

<400> SEQUENCE: 6
cuaacaacau guguggaag ugggt                                             25

<210> SEQ ID NO 7
<211> LENGTH: 27
<212> TYPE: RNA
<213> ORGANISM: Artificial Sequence
<220> FEATURE:
<223> OTHER INFORMATION: SIRNA DIRECTED AGINST MOUSE DEC205

<400> SEQUENCE: 7
acccacuucc acaacauguu guuaguu                                          27

<210> SEQ ID NO 8
<211> LENGTH: 25
<212> TYPE: DNA
<213> ORGANISM: Artificial Sequence
<220> FEATURE:
<223> OTHER INFORMATION: SIRNA DIRECTED AGAINST MOUSE DEC205

<400> SEQUENCE: 8
ggacuuugug cauuuguuaa aggac                                            25

<210> SEQ ID NO 9
<211> LENGTH: 27
<212> TYPE: RNA
<213> ORGANISM: Artificial Sequence
<220> FEATURE:
<223> OTHER INFORMATION: SIRNA DIRECTED AGAINST MOUSE DEC205

<400> SEQUENCE: 9
```

```
guccuuuaac aaaugcacaa aguccuu                                          27

<210> SEQ ID NO 10
<211> LENGTH: 27
<212> TYPE: RNA
<213> ORGANISM: Artificial Sequence
<220> FEATURE:
<223> OTHER INFORMATION: SIRNA DIRECTED AGAINST MOUSE DEC205

<400> SEQUENCE: 10
aagcugaccc ugaaguucau cugcacc                                          27

<210> SEQ ID NO 11
<211> LENGTH: 27
<212> TYPE: RNA
<213> ORGANISM: Artificial Sequence
<220> FEATURE:
<223> OTHER INFORMATION: SIRNA DIRECTED AGAINST MOUSE DEC205

<400> SEQUENCE: 11
ggugcagaug aacuucaggg ucagcuu                                          27

<210> SEQ ID NO 12
<211> LENGTH: 8
<212> TYPE: PRT
<213> ORGANISM: Artificial Sequence
<220> FEATURE:
<223> OTHER INFORMATION: HUMAN OVA PEPTIDE

<400> SEQUENCE: 12

Ser Ile Ile Asn Phe Glu Lys Leu
1               5
```

APTAMER-TARGETTED ANTIGEN DELIVERY

CROSS-REFERENCE TO RELATED APPLICATIONS

This application is a U.S. national stage entry under 35 U.S.C. §371 of PCT International Patent Application No. PCT/US2013/049212, filed Jul. 3, 2013, which claims benefit of U.S. Provisional Application No. 61/671,239, filed Jul. 13, 2012, the contents of each of which are incorporated herein by reference into the subject application.

STATEMENT OF GOVERNMENT SUPPORT

This invention was made with government support under grant numbers AI093539 and AI099567 and awarded by the National Institutes of Health. The government has certain rights in the invention.

BACKGROUND OF THE INVENTION

Throughout this application various publications, patents, patent application publications and books are referred to. Full citations for the publications may be found at the end of the specification. The disclosures of the publications, patents, patent application publications and books are hereby incorporated by reference in their entirety into the subject application to more fully describe the art to which the subject invention pertains.

Poor immunogenicity of conventional protein vaccines, in particular an inability to elicit robust T cell-mediated immunity, has limited their use as vaccines targeting diverse diseases including viral infections and cancers. One approach, which has recently been utilized to activate T cell responses, is targeting of antigen to dendritic cells (DCs), a cell type that is pivotal for eliciting T cell activation. Indeed, DC-targeted approaches have recently attracted significant research interest and are rapidly becoming important therapeutic approaches (1-4). DCs possess the capability of processing self and foreign antigens resulting in presentation of antigen to its cognate T cell receptor. Targeting antigen uptake to DCs via specific DC-enriched receptors has been shown to enhance antigen presentation on major histocompatibility complex (MHC) class I and II molecules by as much as 1000-fold and 50-fold, respectively (5). Depending on the antigenic stimulus, DCs can induce tolerance or activate the immune system (6), making them important targets in the development of novel treatments to autoimmune diseases, viral infections and cancer. Targeting antigens to DCs most often involves coupling the antigen of interest to a delivery agent specific for a readily endocytosed cell surface receptor on the DCs.

Typically, targeted antigen delivery has made use of antibodies as the targeting agent. However, large size and immunogenicity have presented problems in this approach.

The present invention addresses the need to providing improved targeting methods by providing aptamers for preferential vaccine targeting.

SUMMARY OF THE INVENTION

A composition is provided comprising an oligonucleotide aptamer conjugated to an antigen, wherein the aptamer is directed against a cell-surface target of an antigen-presenting cell.

A method is provided of presenting an antigen to a dendritic cell, comprising contacting the dendritic cell with a composition comprising an oligonucleotide aptamer conjugated to the antigen, wherein the aptamer is directed against a cell-surface target of a dendritic cell.

A method is also provided of eliciting an immune response in a subject comprising administering to the subject a composition comprising an oligonucleotide aptamer conjugated to an antigen, wherein the aptamer is directed against a cell-surface target of an antigen-presenting cell, in an amount effective to elicit an immune response.

Additional objects of the invention will be apparent from the description which follows.

BRIEF DESCRIPTION OF THE DRAWINGS

FIG. 1A-1D: Selection and cloning of RNA aptamers against mouse DEC205. (A) Selection scheme. Three rounds of selection were performed against recombinant mDEC205-hIgG1FC fusion protein, with negative selection against hIgG1FC included in rounds 2 and 3. Round 4 was performed against the surface of CHO/mDEC205, while round 5 selected for sequences internalized by mouse BMDC's. See Methods for full procedure. (B) Binding of selection rounds to surface-expressed mDEC205. Individual selection rounds were hybridized with a biotinylated oligonucleotide complementary to a portion of the aptamer pool 3' constant region, incubated with CHO/mDEC205 or CHO cells, counter-stained with SA-PE, and analyzed by flow cytometry. (C) Individual sequences were cloned from round 5 and were used as in b to stain A20.Kb.mDEC205 cells. (D) Sequences of tested round 5 clones. The one non-functional clone, clone 3, is indicated by a '*'. A seven-base motif appearing in most clones is UUCAUAA. CHO—Chinese hamster ovary; CHO/mDEC205—CHO cells transfected to express mouse DEC205; hIgG1FC—FC region of human IgG1; A20.Kb/mDEC205—A20 cells transfected to express mouse Kb and additional mDEC205; SA-PE—streptavidin-phycoerythrin.

FIG. 2A-2D: Specificity of clone 1 for mouse DEC205. (A, B) Knockdown of mDEC205. CHO/mDEC205 cells were treated with two separate siRNA sequences against mDEC205, with siRNA against an unrelated gene (eGFP), or with sham treatment, stained with (A) biotinylated aptamer clone 1 (as in FIG. 1B) or (B) biotinylated antibody clone NLDC145, counterstained with SA-PE, and analyzed by flow cytometry. (C, D) Expression of mDEC205 in related cell lines. A20.Kb and A20.Kb/mDEC205 were stained with (C) biotinylated aptamer clone 1 or round 0 RNA (as in FIG. 1C) or (D) biotinylated antibody clone NLDC145 or isotype rIgG2a antibody, counterstained with SA-PE, and analyzed by flow cytometry. CHO/mDEC205—CHO cells transfected to express mouse DEC205; A20.Kb—A20 cells transfected to express mouse Kb; A20.Kb/mDEC205—A20 cells transfected to express mouse Kb and additional mDEC205; SA-PE—streptavidin-phycoerythrin; rIgG2a—rat IgG2a.

FIG. 8A-8E 6. Mutant forms of min.2 bind DEC205 with lower affinity and are less effective at cross-presentation when compared with min.2. (a) Schematic representation showing min.2 mutation sites. The conserved heptamer is underlined. Mutations are highlighted in red (b) Uptake of fluorescently labeled mutant aptamers by CHO-DEC205 following a 1 hour incubation with 20 nM conjugate as measured by flow cytometry. (c-e) Activation of adoptively transferred OT-I cells following injection of 20 μg multimerized aptamer:OVA or control constructs was determined by their ability to proliferate, as measured by CFSE dilution (c) and intracellular cytokine staining (d, e). Multimerized aptamers conjugated to OVA were injected into B6.SJL-ptprc mice that had received $10^6$ CFSE-labeled OT-I cells. Proliferation and cytokine production of OT-I cells was determined 3 days later by flow cytometry. The percentage of TCRβ+CD45.2+ cells present in the total splenic population (OT-I cells) is reported on each plot. Production of IFNγ (d) and IL2 (e) by OT-I cells. The percentage of OT-I cells that have undergone 3 or more divisions and are producing IFNγ (d) and IL2 (e) is indicated on each dot plot. Data shown are representative of three experiments.

DETAILED DESCRIPTION OF THE INVENTION

Figures 2A, 2B, 2C, 2D:
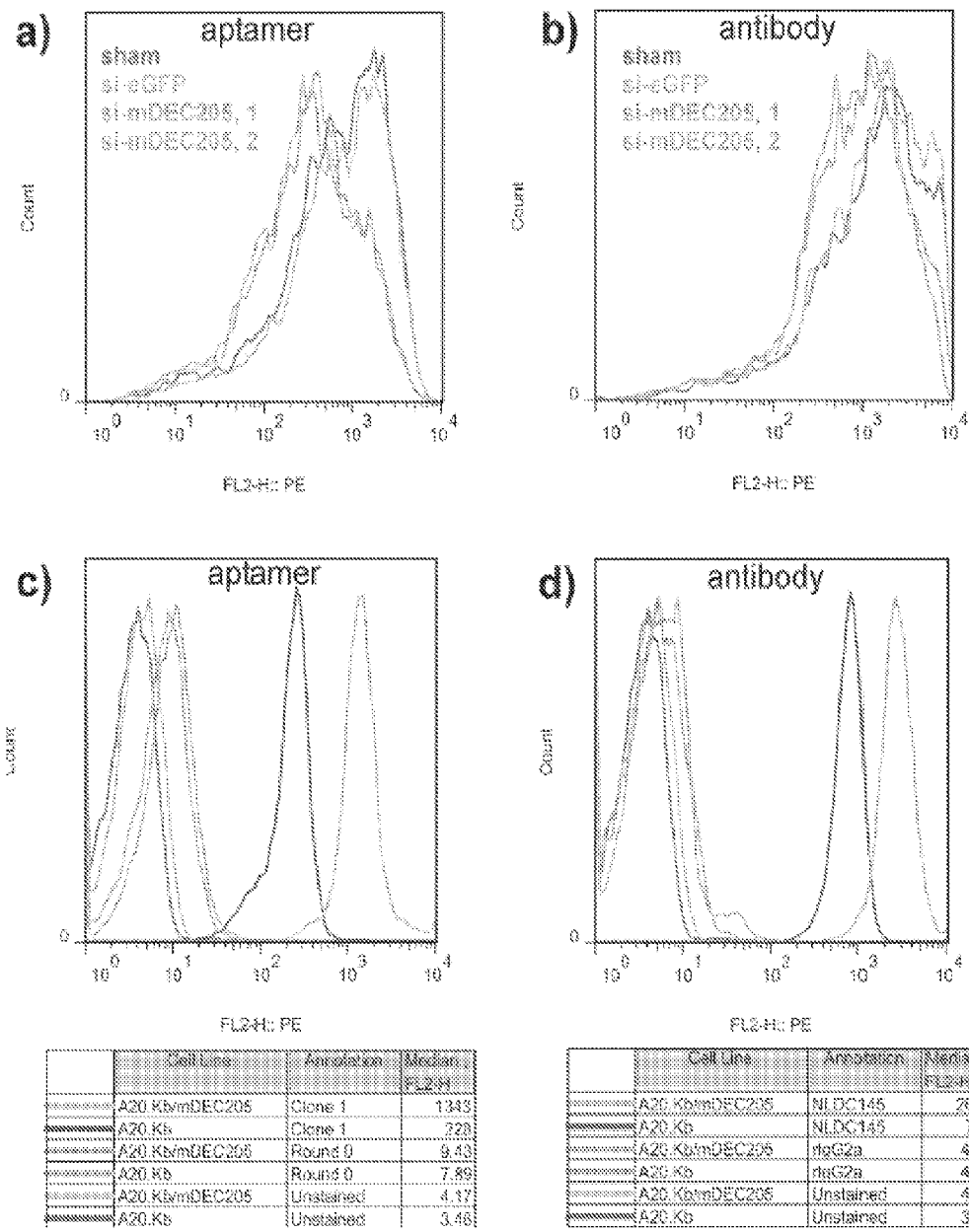

A composition is provided comprising an oligonucleotide aptamer conjugated to an antigen, wherein the aptamer is directed against a cell-surface target of an antigen-presenting cell.

In an embodiment, the aptamer comprises an oligoribonucleotide.

In an embodiment, the aptamer is PEGylated. In an embodiment, the PEG is 200-400 daltons, 400-800 daltons, 800-1000 daltons, 1000-2000 daltons, 2000-5000 daltons, or 5000-10,000 daltons. In an embodiment, the PEG is in the form of a (succinimidyl-[(N-maleimidopropionamido)-dodecaethyleneglycol]ester). In an embodiment, the PEG is in the form of a (succinimidyl-[(N-maleimidopropionamido)-diethyleneglycol]ester), a (succinimidyl-[(N-maleimidopropionamido)-tetraethyleneglycol]ester), a (succinimidyl-[(N-maleimidopropionamido)-hexaethyleneglycol]ester), a (succinimidyl-[(N-maleimidopropionamido)-octaethyleneglycol]ester), or a succinimidyl-[(N-maleimidopropionamido)-tetracosaethyleneglycol]ester).

In an embodiment, the aptamer is multimerized. In an embodiment, the multimerized aptamer comprises 2, 3 or 4 aptamers.

In an embodiment, the antigen-presenting cell is a dendritic cell. In an embodiment, the cell is a CD8alpha+ dendritic cell.

In an embodiment, the aptamer comprises the sequence set forth in SEQ ID NO:1 (GGGAGGUGUGUUAGCACACGAUUCAUAAUCAGCUACCCUCCC). In an embodiment, the aptamer comprises the sequence set forth in SEQ ID NO:1 in the description hereinbelow.

In an embodiment, the aptamer further comprises a 3' inverted dT.

In an embodiment, the antigen is conjugated to the 5' end of the aptamer.

In an embodiment, the antigen is conjugated to the aptamer by a thioether or by a disulfide bond.

In an embodiment, the cell-surface target is a DEC-205 receptor molecule.

In an embodiment, the cell-surface target is a human macrophage mannose receptor.

In an embodiment the aptamer-antigen conjugate further comprises one or more additional oligonucleotide aptamers conjugated to the antigen, wherein the aptamers are directed against the cell-surface target of an antigen-presenting cell.

In an embodiment, the antigen is a vaccine molecule.

In an embodiment, the antigen is a tumor antigen, an autoantigen, or a component of a pathogen.

In an embodiment, the composition further comprises an immunological adjuvant.

In an embodiment, the cell surface target is a DEC-205 receptor having the sequence set forth in GenBank: AAC17636.1.

A method is provided of presenting an antigen to a dendritic cell, comprising contacting the dendritic cell with a composition comprising an oligonucleotide aptamer conjugated to the antigen, wherein the aptamer is directed against a cell-surface target of a dendritic cell.

A method is also provided of eliciting an immune response in a subject comprising administering to the subject a composition comprising an oligonucleotide aptamer conjugated to an antigen, wherein the aptamer is directed against a cell-surface target of an antigen-presenting cell, in an amount effective to elicit an immune response.

In an embodiment of the methods or compositions, the antigen-presenting cell is a dendritic cell. In an embodiment, the cell is a CD8alpha+ dendritic cell.

In an embodiment of the methods or compositions, the aptamer comprises an oligoribonucleotide. In an embodiment, the aptamer is multimerized. In an embodiment, the multimerized aptamer comprises 2, 3 or 4 aptamers. In an embodiment, the aptamer is PEGylated. In an embodiment, the PEG is 200-400 daltons, 400-800 daltons, 800-1000 daltons, 1000-2000 daltons, 2000-5000 daltons, or 5000-10,000 daltons. In an embodiment, the PEG is in the form of a (succinimidyl-[(N-maleimidopropionamido)-dodecaethyleneglycol]ester). In an embodiment, the PEG is in the form of a (succinimidyl-[(N-maleimidopropionamido)-diethyleneglycol]ester), a (succinimidyl-[(N-maleimidopropionamido)-tetraethyleneglycol]ester), a (succinimidyl-[(N-maleimidopropionamido)-hexaethyleneglycol]ester), a (succinimidyl-[(N-maleimidopropionamido)-octaethyleneglycol]ester), or a succinimidyl-[(N-maleimidopropionamido)-tetracosaethyleneglycol]ester).

In an embodiment of the methods or compositions, the antigen is a protein, polypeptide, peptide or carbohydrate. In an embodiment, the antigen is a vaccine molecule. In an embodiment, the antigen is a tumor antigen, an autoantigen, or a component of a pathogen. In an embodiment, the cell-surface target is a receptor molecule. In an embodiment, the cell-surface target is a DEC-205 receptor molecule. In an embodiment, the cell-surface target is a human macrophage mannose receptor. In an embodiment, the composition further comprises an immunological adjuvant. In an embodiment, the cell surface target is a DEC-205 having the sequence set forth in GenBank: AAC17636.1.

In an embodiment of the methods or compositions, the antigen is a peptide of less than 50 amino acids. In an embodiment the antigen is a peptide of less than 45 amino acids. In an embodiment the antigen is a peptide of less than 40 amino acids. In an embodiment the antigen is a peptide of less than 35 amino acids. In an embodiment the antigen is a peptide of less than 30 amino acids. In an embodiment the antigen is a peptide of less than 25 amino acids. In an embodiment the antigen is a peptide of less than 20 amino acids. In an embodiment the antigen is a peptide of less than 15 amino acids. In an embodiment the antigen is a peptide of less than 10 amino acids. In an embodiment the antigen is a peptide of at least 5 amino acids.

In an embodiment of the methods or compositions, the cell surface target is a DEC-205 comprising the following amino acid sequence, or comprising an amino acid sequence having 95% or greater identity to the following amino acid sequence:

(SEQ ID NO: 2)
```
   1 MRTGWATPRR PAGLLMLLFW FFDLAEPSGR AANDPFTIVH
     GNTGKCIKPV YGWIVADDCD

61 ETEDKLWKWV SQHRLFHLHS QKCLGLDITK SVNELRMFSC
     DSSAMLWWKC EHHSLYGAAR

121 YRLALKDGHG TAISNASDVW KKGGSEESLC DQPYHEIYTR
     DGNSYGRPCE FPFLIDGTWH

181 HDCILDEDHS GPWCATTLNY EYDRKWGICL KPENGCEDNW
     EKNEQFGSCY QFNTQTALSW

241 KEAYVSCQNQ GADLLSINSA AELTYLKEKE GIAKIFWIGL
     NQLYSARGWE WSDHKPLNFL

301 NWDPDRPSAP TIGGSSCARM DAESGLWQSF SCEAQLPYVC
     RKPLNNTVEL TDVWTYSDTR

361 CDAGWLPNNG FCYLLVNESN SWDKAHACKC AFSSDLISIH
     SLADVEVVVT KLHNEDIKEE

421 VWIGLKNINI PTLFQWSDGT EVTLTYWDEN EPNVPYNKTP
     NCVSYLGELG QWKVQSCEEK

481 LKYVCKRKGE KLNDASSDKM CPPDEGWKRH GETCYKIYED
     EVPFGTNCNL TITSRFEQEY

541 LNDLMKKYDK SLRKYFWTGL RDVDSCGEYN WATVGGRRRA
     VTFSNWNFLE PASPGGCVAM

601 STGKSVGKWE VKDCRSFKAL SICKKMSGPL GPEEASPKPD
     DPCPEGWQSF PASLSCYKVF

661 HAERIVRKRN WEEAERFCQA LGAHLSSFSH VDEIKEFLHF
     LTDQFSGQHW LWIGLNKRSP

721 DLQGSWQWSD RTPVSTIIMP NEFQQDYDIR DCAAVKVFHR
     PWRRGWHFYD DREFIYLRPF

781 ACDTKLEWVC QIPKGRTPKT PDWYNPDRAG IHGPPLIIEG
     SEYWFVADLH LNYEEAVLYC

841 ASNHSFLATI TSFVGLKAIK NKIANISGDG QKWWIRISEW
     PIDDHFTYSR YPWHRFPVTF

901 GEECLYMSAK TWLIDLGKPT DCSTKLPFIC EKYNVSSLEK
     YSPDSAAKVQ CSEQWIPFQN

961 KCFLKIKPVS LTFSQASDTC HSYGGTLPSV LSQIEQDFIT
     SLLPDMEATL WIGLRWTAYE

1021 KINKWTDNRE LTYSNFHPLL VSGRLRIPEN FFEEESRYHC
     ALILNLQKSP FTGTWNFTSC

1081 SERHFVSLCQ KYSEVKSRQT LQNASETVKY LNNLYKIIPK
     TLTWHSAKRE CLKSNMQLVS

1141 ITDPYQQAFL SVQALLHNSS LWIGLFSQDD ELNFGWSDGK
     RLHFSRWAET NGQLEDCVVL
```

-continued

```
1201  DTDGFWKTVD  CNDNQPGAIC  YYSGNETEKE  VKPVDSVKCP
      SPVLNTPWIP  FQNCCYNFII

1261  TKNRHMATTQ  DEVHTKCQKL  NPKSHILSIR  DEKENNFVLE
      QLLYFNYMAS  WVMLGITYRN

1321  NSLMWFDKTP  LSYTHWRAGR  PTIKNEKFLA  GLSTDGFWDI
      QTFKVIEEAV  YFHQHSILAC

1381  KIEMVDYKEE  HNTTLPQFMP  YEDGIYSVIQ  KKVTWYEALN
      MCSQSGGHLA  SVHNQNGQLF

1441  LEDIVKRDGF  PLWVGLSSHD  GSESSFEWSD  GSTFDYIPWK
      GQTSPGNCVL  LDPKGTWKHE

1501  KCNSVKDGAI  CYKPTKSKKL  SRLTYSSRCP  AAKENGSRWI
      QYKGHCYKSD  QALHSFSEAK

1561  KLCSKHDHSA  TIVSIKDEDE  NKFVSRLMRE  NNNITMRVWL
      GLSQHSVDQS  WSWLDGSEVT

1621  FVKWENKSKS  GVGRCSMLIA  SNETWKKVEC  EHGFGRVVCK
      VPLGPDYTAI  AIIVATLSIL

1681  VLMGGLIWFL  FQRHRLHLAG  FSSVRYAQGV  NEDEIMLPSF
      HD
```

In an embodiment of the methods or compositions, the aptamer is less than 60, less than 50, less than 40 or less than 30 nucleotides in length.

Aptamers, unless otherwise specified, are RNA or DNA molecules, or comprise both ribonucleotide residues and deoxyribonucleotide residues, and are generally generated from large combinatorial libraries ($10^{14}$-$10^{15}$) of nucleic acids. In an embodiment, the aptamer comprises RNA. This may be done by a process of in vitro selection or by SELEX (Systematic Evolution of Ligands by Exponential Enrichment) which targets a specific protein or molecular target. They are generated though a process that relies on binding. Aptamers are thus nucleic acids (oligonucleotides, often oligoribonucleotides—a ribonucleic acid aptamer) which bind a specific protein or molecular target, typically with nanomolar or subnanomolar affinity. Generally, aptamers discriminate against molecules closely related to the target molecule.

The aptamers of the invention may comprise nucleosides. A "nucleoside" as used herein is a glycosylamine consisting of a base bound to a ribose or deoxyribose sugar via a beta-glycosidic linkage. Examples include cytidine, uridine, adenosine, guanosine, thymidine and inosine. Nucleosides can be phosphorylated by specific kinases in the cell on the sugar's primary alcohol group (—$CH_2$—OH), producing nucleotides, which are the molecular building blocks of DNA and RNA. Nucleosides can be produced by de novo synthesis pathways, particularly in the liver, but they are more abundantly supplied via ingestion and digestion of nucleic acids in the diet, whereby nucleotidases break down nucleotides (such as the thymine nucleotide) into nucleosides (such as thymidine) and phosphate.

The aptamers of the invention may comprise nucleoside analogs. A "nucleoside analog" is a nucleoside structurally similar to the naturally occurring residues in RNA and DNA, used in medicine and in molecular biology, and which can be incorporated, e.g. chemically, into an oligonucleotide or nucleic acid by formation of a phosphodiester bond or equivalent with one or two residues of the residue chain depending on whether the nucleoside analog is in a terminal or intra-chain position, respectively. Nucleic acids are chains of nucleotides, which are composed of three parts: a phosphate backbone, a pucker-shaped pentose sugar, either ribose or deoxyribose, and one of five nucleobases. A nucleoside analogue differs from a nucleoside by having any one or more of its hydroxyl, base or sugar groups altered, as long as the alteration does not prevent the nucleoside analogue from being incorporated into an oligonucleotide such as an aptamer, internalizing nucleic acid or tumor-homing nucleic acid. In an embodiment of the invention the nucleoside analogue(s) are one or more of the following: a deoxyadenosine analog, a deoxycytidine analog, a deoxyguanosine analog, a (deoxy-)thymidine analog, and/or a deoxyuridine analog. Typically the analogue nucleobases confer, among other things, different base pairing and base stacking proprieties. The ribonucleic acid aptamers of the invention may thus comprise nucleoside analogs.

Nucleoside analogs as envisaged in the current invention include, but are not limited to, cytosine arabinoside, fludarabine, cladribine, acyclovir, 2',3'-dideoxyinosine; 9-β-D-ribofuranosyladenine; β-arabinofuranosylcytosine; arabinosylcytosine; 4-amino-5-fluoro-1-[(2R,5S)-2-(hydroxymethyl)-1,3-oxathiolan-5-yl]-1,2-dihydropyrimidin-2-one; 2',3'-dideoxy-3'-thiacytidine; 2'-3'-dideoxycytidine; {(1S, 4R)-4-[2-amino-6-(cyclopropylamino)-9H-purin-9-yl]cyclopent-2-en-1-yl}methanol; 2-Amino-9-[(1S,3R,4S)-4-hydroxy-3-(hydroxymethyl)-2-methylidenecyclopentyl]-6,9-dihydro-3H-purin-6-one; 2'-3'-didehydro-2'-3'-dideoxythymidine; 1-(2-deoxy-β-L-erythro-pentofuranosyl)-5-methylpyrimidine-2,4(1H,3H)-dione; 1-[(2R,4S,5S)-4-azido-5-(hydroxymethyl)oxolan-2-yl]-5-methylpyrimidine-2,4-dione; 1-[(2R,4S,5R)-4-hydroxy-5-(hydroxymethyl)oxolan-2-yl]-5-iodo-1,2,3,4-tetrahydropyrimidine-2,4-dione; 1-[4-hydroxy-5-(hydroxymethyl)oxolan-2-yl]-5-(trifluoromethyl) pyrimidine-2,4-dione; 5-Fluoro-2'-deoxycytidine; 5-Fluorodeoxycytidine; Floxuridine (5-Fluoro-1-[4-hydroxy-5-(hydroxymethyl)tetrahydrofuran-2-yl]-1H-pyrimidine-2,4-dione); 4-amino-1-(2-deoxy-2,2-difluoro-β-D-erythro-pentofuranosyl)pyrimidin-2(1H)-one; 2',2'-difluoro-2'-deoxycytidine; (8R)-3-(2-deoxy-β-D-erythro-pentofuranosyl)-3,4,7,8-tetrahydroimidazo[4,5-d][1,3]diazepin-8-ol.

The ribonucleic acid aptamers of the invention may comprise, on their constituent nucleotides, 2' modifications. Preferred modifications are 2' F on pyrimidines and 2' H or 2' OMe on purines.

In an embodiment, of the methods, compositions and aptamers described herein, the aptamer comprises SEQ ID NO:1 with 0, 1, 2, 3, 4, 5, 6, 7, 8, 9, or 10 additional nucleotide residues at the 3' end thereof, and, independently, 0, 1, 2, 3, 4, 5, 6, 7, 8, 9, or 10 additional nucleotide residues at the 5' end thereof.

The present invention provides aptamers that are ribonucleic acid or deoxyribonucleic acid or mixed ribonucleic acid and deoxyribonucleic acid or which are analogs thereof, especially via modification of 2' groups on purines and/or pyrimidines. Aptamers of the invention may be single stranded. In some embodiments, the aptamers of the invention comprises at least one chemical modification (other than the included nucleoside analog(s), if included). In some embodiments, the chemical modification is selected from the group consisting of: a chemical substitution at a sugar position; a chemical substitution at a phosphate position; and a chemical substitution at a base position, of the nucleic acid. In other embodiments, the chemical modification is selected from the group consisting of: incorporation of a modified nucleotide, 3' capping, conjugation to a high molecular weight, non-immunogenic compound, conjugation to a lipophilic compound, and incorporation of phosphorothioate into the phosphate back bone. In a preferred embodiment, the non-immunogenic, high molecular weight compound is polyalkylene glycol, more preferably polyethylene glycol. In an embodiment the chemical modification is an inverted thymidine cap. In an embodiment the chemical modification is once or more phosphorothioate backbone modification(s). In a preferred embodiment, the aptamer is modified at a 2' group of one or more purines thereof and/or at a 2' of one or more pyrimidines thereof.

Aptamers of the present invention can be administered by any appropriate route or means, including systemically, topically, parentally or enterally. In non-limiting examples, administration is by subcutaneous injection (aptamer bioavailability via subcutaneous administration is >80% in monkey studies (Tucker et al., *J. Chromatography* B. 732: 203-212, (1999)), intravenously, intranasally (lower and/or upper epithelia), or by direct injection into the desired body system, tissue or organ. Any vaccine dosing schedule may be employed, including those used in the art for the administration of the aptamer-antigen conjugates of the present invention.

The present invention additionally provides a pharmaceutical composition comprising a therapeutically effective amount of the aptamer-antigen composition and a pharmaceutically acceptable carrier.

The pharmaceutically acceptable carrier is preferably compatible with the aptamer-antigen conjugate and not significantly deleterious to the subject. Examples of acceptable pharmaceutical carriers include liposomes (which may encapsulate the aptamer-antigen conjugate, or which may be attached the aptamer-antigen conjugate) saline, carboxymethylcellulose, crystalline cellulose, glycerin, gum arabic, lactose, magnesium stearate, methylcellulose, powders, saline, sodium alginate, sucrose, starch, talc, and water, among others. Formulations of the pharmaceutical composition may conveniently be presented in unit dosage and may be prepared by any method known in the pharmaceutical art. For example, the aptamer, or aptamer conjugate or aptamer-liposome composition may be brought into association with a carrier or diluent, as a suspension or solution. Optionally, one or more accessory ingredients, such as buffers, flavoring agents, surface-active ingredients, and the like, may also be added. The choice of carriers will depend on the method of administration. The pharmaceutical composition can be formulated for administration by any method known in the art, including but not limited to, intravenously and orally. In one embodiment, there may be a number of active pharmaceutical ingredients in the formulation or composition aside from the aptamer-antigen conjugate. In this embodiment, the other active pharmaceutical ingredients in the formulation or composition must be compatible with the aptamer.

The aptamers of the invention can be chemically synthesized if desired, or transcribed from appropriate encoding nucleic acids and modified during or after sequence synthesis if desired. The aptamers of the present invention, with or without included one or more nucleoside analogs, can be stored in a variety of forms, including as lyophilized powders.

The term "antigen" means all, or parts, of a protein, polypeptide, peptide or carbohydrate, and/or vaccine molecule capable of causing an immune response in a vertebrate, preferably a mammal. In an embodiment, the antigen is a protein, polypeptide or peptide. In a further embodiment, the protein, polypeptide or peptide may be glycosylated. In an embodiment, the antigen is a vaccine molecule. A "vaccine molecule" as used herein is a chemical molecule capable of eliciting an immune response in an animal, preferably a mammal, when administered thereto as a vaccine. In non-limiting examples, the vaccine molecule is an intact but inactivated (non-infective) or attenuated form of a biological pathogen, a purified or isolated component of a biological pathogen that is immunogenic (e.g., an outer coat protein of a virus), a toxoids (e.g. a modified tetanospasmin toxin of tetanus which is non-toxic itself).

In an embodiment of the methods, T cell stimulation is effected. In an embodiment of the methods, CD8+ T cell stimulation is effected.

In an embodiment, the immune response comprises a Th1 response. In an embodiment, the immune response comprises an adaptive immunity response. In an embodiment, the immune response comprises interferon gamma production. In an embodiment, the immune response comprises interleukin-2 production. In an embodiment, the immune response comprises T-cell proliferation. In an embodiment, the composition is administered in an amount sufficient to induce cytokine release by dendritic cells. In an embodiment, the method evokes an immune response comprising presentation of the antigen as a component of an MHC-I or MHC-II conjugate. n an embodiment, the immune response is an adaptive immunity response.

Antigen-presenting cells are well-known in the art, and are generally considered as cells of the immune system that displays foreign antigen complexes with major histocompatibility complex (MHC) on their surfaces. Examples include dendritic cells, macrophages and B-cells. In a preferred embodiment of the invention, the antigen-presenting cell is of the same species as the subject.

As used herein "and/or", for example as in option A and/or option B, means the following embodiments: (i) option A, (ii) option B, and (iii) the option A plus B, and any subset of such options, including only one option.

The subject may be any subject. Preferably, the subject is a mammal More preferably, the subject is a human.

All combinations of the various elements described herein are within the scope of the invention unless otherwise indicated herein or otherwise clearly contradicted by context.

Where a numerical range is provided herein, it is understood that all numerical subsets of that range, and all the individual integers contained therein, are provided as part of the invention. Thus, for example, an oligonucleotide which is less than 30 nucleotides in length includes the subset of oligonucleotides which are 18 to 22 nucleotides in length, the subset of oligonucleotides which are 20 to 25 nucleotides in length etc. as well as an oligonucleotide which is 10 nucleotides in length, an oligonucleotide which is 11 nucleotides in length, an oligonucleotide which is 12 nucleotides in length, etc. up to and including an oligonucleotide which is 29 nucleotides in length. This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

Effective therapeutic vaccines often require activation of T cell-mediated immunity. However, poor immunogenicity of conventional protein-based vaccines has necessitated the development of alternative approaches. Robust T cell activation can be achieved by using antibodies or antibody fragments to direct antigens of interest to professional antigen presenting cells. Here, aptamers have been selected that specifically bind DEC205, a C-type lectin expressed predominantly on the surface of CD8α+ dendritic cells (DCs) that has been shown to be particularly efficient at facilitating antigen cross-presentation and subsequent CD8+ T cell activation. A minimized DEC205 aptamer was conjugated to the model antigen ovalbumin (OVA), and the DEC205 aptamer-OVA conjugate was delivered in vitro to murine CD11c+ splenocytes. Antigen cross-presentation was verified by proliferation and cytokine production by primary murine CD8+ T cells expressing a T cell receptor (TCR) specific for the MHC I-restricted OVA257-264 peptide SIINFEKL (SEQ ID NO:12). Compared with a nonspecific modified RNA of similar length, DEC205 aptamer-OVA-mediated antigen delivery stimulated strong proliferation and interferon gamma (IFNγ) secretion.

Nucleic acid aptamers, however, due to their unique chemical properties and low immunogenicity, may provide an effective alternative to antibody-based antigen delivery (7,8). Aptamers are short ribonucleic acid (RNA) or deoxyribonucleic acid (DNA) sequences generated in vitro by an iterative selection process (systematic evolution of ligands by exponential enrichment, SELEX) to bind with high affinity and specificity to a given target. Aptamers have demonstrated a wide range of flexibility, finding applications in flow cytometry staining, activating signaling pathways through cell surface receptor ligation, drug or siRNA delivery, blocking protein-protein interactions, and inhibiting enzyme function (7-9). Several aptamer-based therapeutics are currently undergoing clinical trials, with one already approved for use (10).

Results

With the goal of utilizing aptamers for targeted antigen delivery, herein are disclosed aptamers that recognize the murine receptor DEC205 (mDEC205) and are adapted for use as a targeted antigen delivery agent. DEC205 is an excellent target receptor for this proof of principle study. This C-type lectin is expressed mainly by CD8α+DCs, with lower expression by other cells in the hematopoietic lineage (>1 log less)(11). More importantly, studies targeting this receptor with anti-DEC205 antibodies fused to a variety of different antigens have demonstrated that targeting this receptor leads to efficient cross-presentation of these molecular cargoes including cancer (12,13) and HIV epitopes (14,15). Indeed, a cancer vaccine utilizing anti-human DEC205 antibody is already being tested in the clinic (16).

A sequential selection strategy of recombinant mDEC205 protein followed by cells expressing mDEC205 was used to identify nuclease stabilized RNA aptamers specific for the mDEC205 receptor. Minimized aptamers conjugated to the model chicken antigen ovalbumin (OVA) specifically bound mDEC205-expressing cell lines and primary cells. In the presence of the adjuvants lipopolysaccharide (LPS) and polyinosinic:polycytidylic acid (poly(I:C)), incubation of anti-DEC205 aptamer-OVA conjugate with primary DCs in vitro resulted in cross presentation of antigen, as determined by T cell proliferation assays and cytokine secretion.

Identification of Anti-mDEC205 Aptamers: Pool enrichment—In order to identify aptamers that specifically recognized mDEC205 and that were readily internalized by cells that naturally express this receptor, a three-stage selection procedure was employed (FIG. 1a). Starting with an initial 2'-fluoro-pyrimidine-modified RNA library encompassing ~$10^{14}$ unique sequences, three rounds of selection were performed utilizing a recombinant mDEC205-hIgGF$_C$ fusion protein produced in CHO cells. Surprisingly, when each round of the selection against CHO/mDEC205 cells was assayed (a CHO cell line engineered to over-express mDEC205) by flow cytometry, the Round 3 population already showed marked staining (FIG. 1b). Importantly, no apparent staining was observed when the assay was repeated with the parental CHO cells (FIG. 1b).

In order to further enrich the population for aptamers that bound to the receptor in the context of the cell surface, for Round 4 a cell-based selection utilizing CHO/mDEC205 cells was switched to. Prior to the selection, a negative selection step was performed on CHO cells to deplete the population of any nonspecific cell binders. Following positive selection on CHO/mDEC205 cells, bound RNA was recovered amplified and assayed by flow cytometry.

The Round 4 RNA showed no improvement over Round 3 (FIG. 1b), which prompted us to turn an additional round with further modification to the selection scheme. For this, bone marrow-derived dendritic cells (BMDCs) were targeted, a model for 'classic' CD11c$^+$ DCs, which express mDEC205 and are capable of antigen cross-presentation (17,18). The goal was to ensure that the selected aptamers could bind their target receptor and be efficiently internalized. Therefore, following a one-hour incubation with the aptamer library in media, the cells were stringently washed with buffer followed by acidic glycine to remove surface bound molecules. Finally, the cells were trypsinized and then treated with an RNAse cocktail to ensure that only RNAs that had been internalized by the cells were recovered. As shown in FIG. 1b, when assayed on CHO/mDEC205 cells, the Round 5 population showed significant improvement over Round 4.

Clone analysis: Flow cytometric analysis (FIG. 1c) of individual clones identified from Round 5 (FIG. 1d) revealed that all clones bound CHO/mDEC205, but not CHO cells, with the exception of Clone 3, which proved nonfunctional. Interestingly, two clones that showed some of the best activity (Clones 1 and 15) possessed identical random regions, with the only difference being that the Clone 1 sequence lacked a significant portion of the 3'-constant region present in Clone 15 and the rest of the library. This deletion did not affect its ability to stain CHO/mDEC205 cells by flow cytometry (FIG. 1c). The reduced Clone 1 proved a good starting point to confirm specificity and to generate a minimized construct that would be amenable to chemical synthesis and that would facilitate chemical conjugation.

In order to verify the specificity of the selected aptamers for mDEC205, the expression of mDEC205 was knocked down on CHO/mDEC205 cells using siRNA and assessed the level of surface staining 24 hrs later using either an mDEC205-specific antibody, NLDC145, or the anti-mDEC205 aptamer, Clone 1. Cells treated with the anti-DEC205 siRNA displayed a ~50% knockdown in protein expression as determined by flow cytometry, with the data generated using the aptamer, Clone 1 paralleling those of the antibody (FIGS. 2A and B). Importantly, no change in the expression levels of DEC205 was observed when cells were treated with a non-targeted siRNA (control siRNA) or transfection agent alone. No significant cell staining was observed when similar experiments were conducted using an isotype control antibody, or a non-targeting aptamer.

In addition, the ability of Clone 1 to bind A20.Kb cells, a B cell lymphoma line that natively expresses mDEC205, was investigated as well as A20.Kb/mDEC205 cells, a variant of A20.Kb cells engineered to express higher levels of mDEC205. As expected, when treated with the aptamer, A20.Kb cells showed significant staining as determined by flow cytometry with even greater levels observed for the A20.Kb/mDEC205 cells (FIG. 2c). These results paralleled the surface staining experiments performed with NLDC145 (FIG. 2d). Taken together, these data indicated that the Clone 1 is capable of detecting and binding mDEC205 in a manner similar to that of the NLDC145 antibody clone.

Minimization: Sequence analysis of the Round 5 clones revealed a seven base sequence (5'-UUCAUAA-3') (SEQ ID NO:3) that recurred in several clones (FIG. 1d) and often formed a short loop when the constructs were folded. Further analysis of Clones 1 and the full-length Clone 15 prompted us to design and test a series of successive truncations aimed at preserving this sequence but minimizing the overall size of the aptamer. Truncation constructs were generated by transcription and all shared a common hybridization handle, which facilitated analysis by flow cytometry. A functional analysis of these variants resulted in the identification of a minimized sequence composed of a 42-nucleotide aptamer core, 'min.2' which performed better than the bulk Round 5 pool.

Figures 3A, 3B:
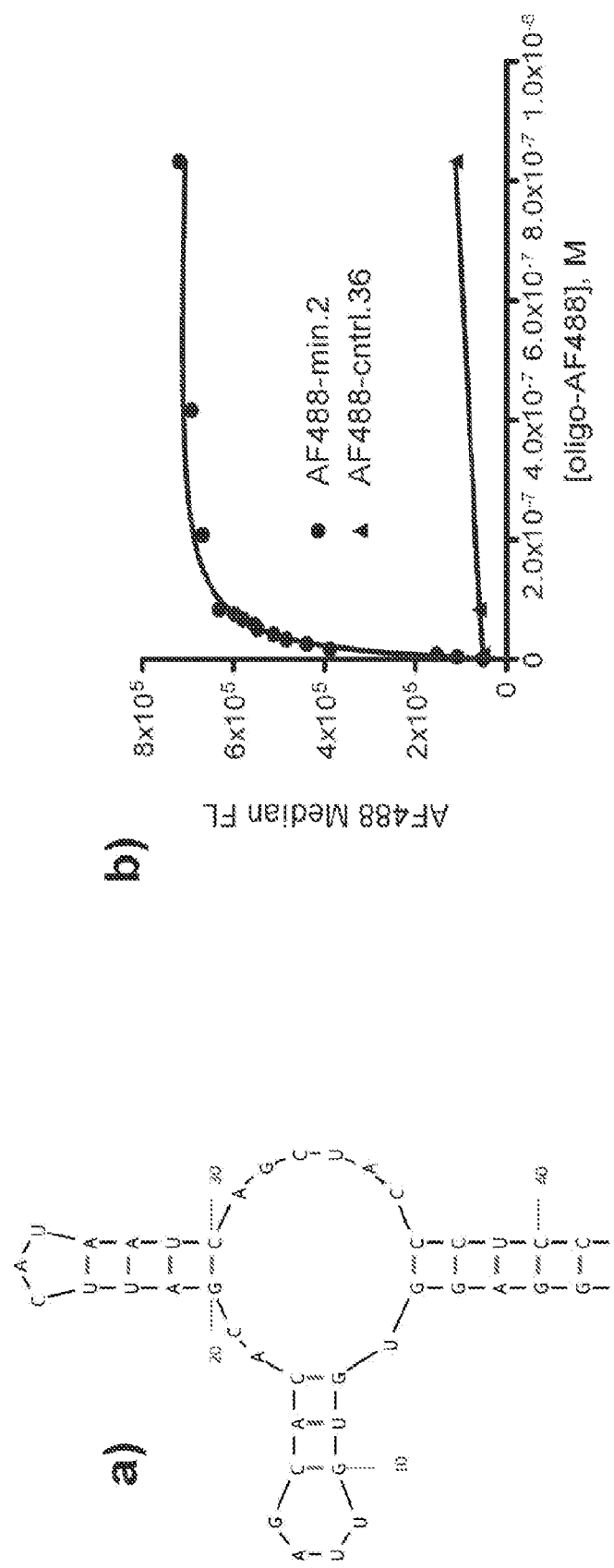
FIG. 3A-3B: Minimized clone 1 and its affinity for surface-expressed mouse DEC205. (A) Mfold-predicted secondary structure of minimized clone 1 ('min.2'). (B) Binding curve of min.2 for surface-expressed mDEC205. Min.2 and a nonspecific control sequence of similar length ('cntrl.36') were chemically synthesized, conjugated to Alexa Fluor 488, and used at several concentrations to stain A20.Kb/mDEC205 cells. Median fluorescence values were used in GraphPad Prism to calculate a dissociation constant, KD, of 23±6 nM. AF488—Alexa Fluor 488. A20.Kb/mDEC205—A20 cells transfected to express mouse Kb and additional mDEC205.

The minimized aptamer, min.2 (FIG. 3a), was chemically synthesized bearing a 3' inverted dT for added serum stability and a 5' thiol to facilitate subsequent chemical conjugations. When labeled with Alexa Fluor 488, this chemically synthesized aptamer performed as well as constructs produced by transcription (data not shown). Direct labeling of min.2 also allowed us to measure the apparent dissociation constant of this aptamer for cell-surface mDEC205 on A20 cells (23±6 nM; FIG. 3b). The specificity of Clone 1 and high affinity of its minimized form, min.2, constitute a promising basis for using this aptamer for targeted antigen delivery.

Enhancing Cross Presentation with Anti-mDEC205 Aptamers: Aptamer-OVA conjugation—Antibodies that target DEC205 have been shown to greatly enhance the cross-presentation of antigens (5,6,19). To this end the well characterized ovalbumin (OVA) system was utilized as a model to investigate the ability of min.2 to deliver cargo for cross-presentation.

Figures 4A, 4B, 4C:
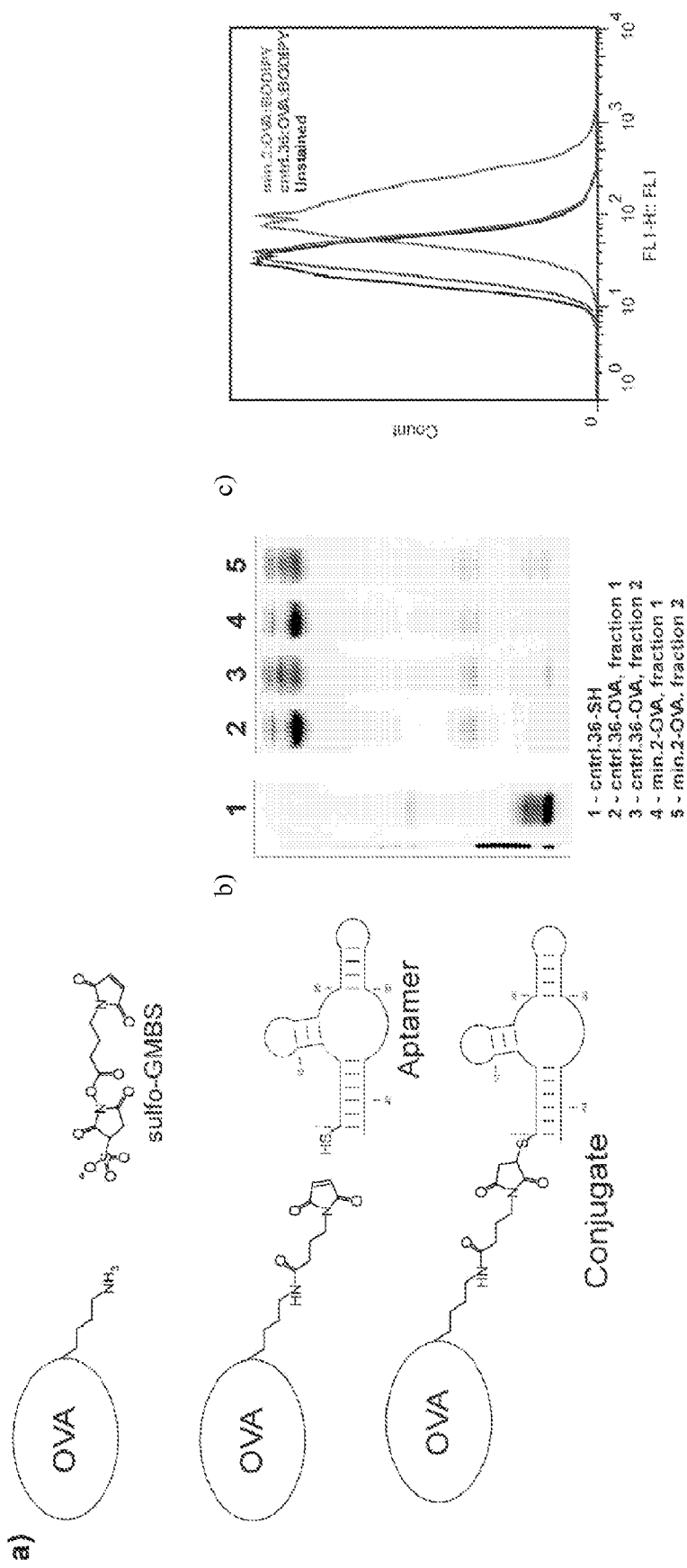
FIG. 4A-4C: RNA-OVA conjugation. (A) Conjugation scheme. The crosslinker sulfo-GMBS was used to chemically conjugate OVA to min.2. See Methods for full procedure. Cntrl.36 was conjugated to OVA in a similar manner. RNA-OVA conjugates were purified by anion exchange chromatography on a Mini Q™ 4.6/50 PE column. Fractions 1 and 2 were collected for further analysis. (B) PAGE analysis of purification. Conjugate fractions 1 and 2 from cntrl.36-OVA and min.2-OVA purifications were analyzed on a 7 M urea, 8% acrylamide PAGE gel and compared with unconjugated cntrl.36. (C) Cell surface staining with conjugates. BODIPY FL-labeled conjugates were compared to FITC-labeled min.2 for staining CHO/mDEC205. PAGE, polyacrylamide gel electrophoresis; CHO/mDEC205—CHO cells transfected to express mouse DEC205; OVA—ovalbumin; min.2,cntrl.36:OVA:BODIPY-BODIPY FL-labeled RNA-OVA conjugates.

Using the 5'-thiol-modified min.2, aptamer-OVA conjugates were generated using the heterobifunctional cross-linker N-[γ-maleimidobutyryloxy]sulfosuccinimide ester (sulfo-GMBS). In short, OVA protein was activated by reaction with a 10-fold molar excess of sulfo-GMBS. The activated OVA was subsequently desalted and then reacted with the 5'-thiolated min.2 in a ratio of 5:1 OVA:RNA (FIG. 4a). The resulting conjugate, min.2:OVA, was subsequently purified by anion exchange HPLC. The conjugate eluted at two distinct, but overlapping, times (FIG. 4b), which likely represent single- or double-aptamer-conjugated OVA. Subsequent experiments were performed using the first fraction, which consisted largely of a single (>85%) major species as determined by gel electrophoresis (FIG. 4c).

As a control to ensure the specificity of min.2-mediated antigen delivery, an RNA of similar length but unrelated sequence ('cntrl.36') was chemically synthesized and conjugated to OVA in a manner similar to that of min.2. Conjugation efficiency and purification of cntrl.36 was very similar to that of min.2, indicating that likely the only significant difference between the two conjugates is the RNA sequence itself (FIG. 4c).

To ensure that the aptamer-protein conjugates still functioned, fluorescently labeled conjugates were generated and assessed binding to CHO/mDEC205 cells. As shown in FIG. 4d, BODIPY FL-labeled min.2:OVA stained CHO/mDEC205 cells significantly more than did BODIPY FL-labeled cntrl.36:OVA.

Aptamer-Mediated OVA Delivery: The ability of anti-mDEC205 aptamer to enhance delivery and cross presentation was assessed in vitro using murine CD11c$^+$ splenocytes, a subset of which are CD8α$^+$DEC205$^+$. In short, DCs were incubated with either the aptamer-OVA conjugates (min.2:OVA or cntrl.36:OVA) or antibody-OVA fusions (NLDC145:OVA or GL117:OVA, a rat IgG2a anti-*Escherichia coli* β-galactosidase antibody which served and an isotype control).

CD69 is expressed within hours of T cell stimulation (20), making it one of the earliest cell surface markers to be upregulated and a useful indicator of T cell activation. Cytometric analysis of lymph node cells isolated from RAG1$^{-/-}$ OT-I$^{+/+}$ ('OT-I cells') exposed to DC's treated with as little as 10 nM min.2:OVA for ~20 hrs demonstrated the potential for this aptamer to induce T cell activation, although the observed effect was less than that seen with the mDEC205-targeted antibody-OVA chimera, NLDC145:OVA (FIG. 5A).

Figures 5A, 5B, 5C:
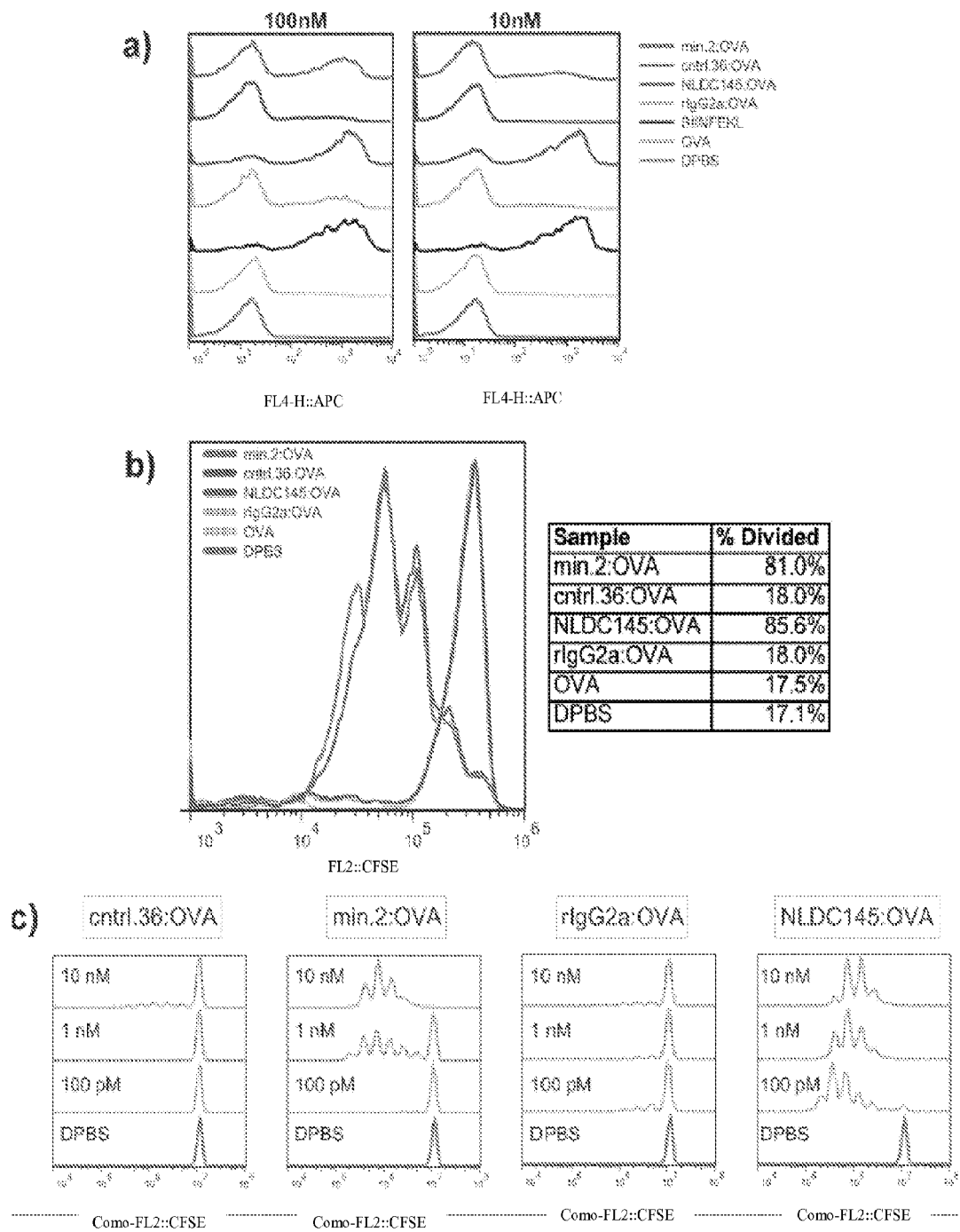
FIG. 5A-5C: RNA-OVA conjugate-induced proliferation. (A) CD69 activation of OT-I cells following incubation with 100 nM or 10 nM antigen-treated CD11c+ splenocytes. (B) Day 2 proliferation. CFSE-labeled OT-I cells were incubated for two days with 10 nM antigen-treated CD11c+ splenocytes from C57BL/6 mice and analyzed by flow cytometry for proliferation. See Methods for full procedure. Percentage of OT-I cells entering cell division was calculated by FlowJo (TreeStar). (C) Antigen titration. Experiment was performed as in (B), but at different concentrations (10 nM, 1 nM and 100 pM) of antigen. OVA—ovalbumin; NLDC145,rIgG2a:OVA—recombinant fusion of OVA and anti-mDEC205 antibody clone NLDC145 or isotype rat IgG2a antibody; min.2,cntrl.36:OVA—OVA chemically conjugated to min.2 or cntrl.36 RNA.

A much more dramatic effect was observed when the effect on OT-I cell proliferation was examined (FIG. 5B). Using CFSE-labeled OT-I cells, T cell proliferation was monitored two or three days following exposure to treated DCs. Targeting antigens with either the mDEC205-specific aptamer-OVA conjugate (min.2:OVA) or antibody-OVA chimera (NLDC145:OVA) induced a strong activation response, with most cells (>80%) dividing after two days, whereas incubations performed with the nonspecific RNA conjugate (cntrl.36:OVA) or isotype antibody chimera (rIgG2a:OVA) resulted in minimal T cell division, similar to the DPBS-treated control (FIG. 5B). When similar experiments were performed at decreasing concentrations of targeting ligand, significant enhancement of cross-presentation was observed for the anti-mDEC205 aptamer conjugate min.2:OVA at concentrations as low as 1 nM (FIG. 5C). Proliferation continued for at least an additional day and was also observed when similar experiments were performed with CD11c$^+$ splenocytes prepared from Flt3L-treated mice.

Activation of naïve T cells results in acquisition of effector functions including expression of activation markers, cell proliferation and cytokine production. Intracellular cytokine flow cytometry (ICFC) was used to measure interleukin 2 (IL-2) and interferon gamma (IFNγ) present in OT-I T cells following incubation with DCs treated with aptamer conjugates or antibody chimeras. Significant intracellular IL-2 and IFNγ was observed for OT-I cells in response to OVA delivery by aptamer or antibody, and was similar to the response seen with SIINFEKL peptide (FIG. 6a,b) (SEQ ID NO:12). The response to each nonspecific control reagent included a subpopulation with moderately increased staining for intracellular IL-2 and IFNγ. This result is similar to previously reported findings6 and does not correlate with specific aptamer/antibody-mediated OT-I proliferative responses (FIG. 5b). In contrast, the incubation of CD11c+ splenocytes with the same amount of soluble OVA did not elicit any subpopulation with increased staining for intracellular IFNγ and IL-2.

Figures 6A, 6B, 6C, 6D:
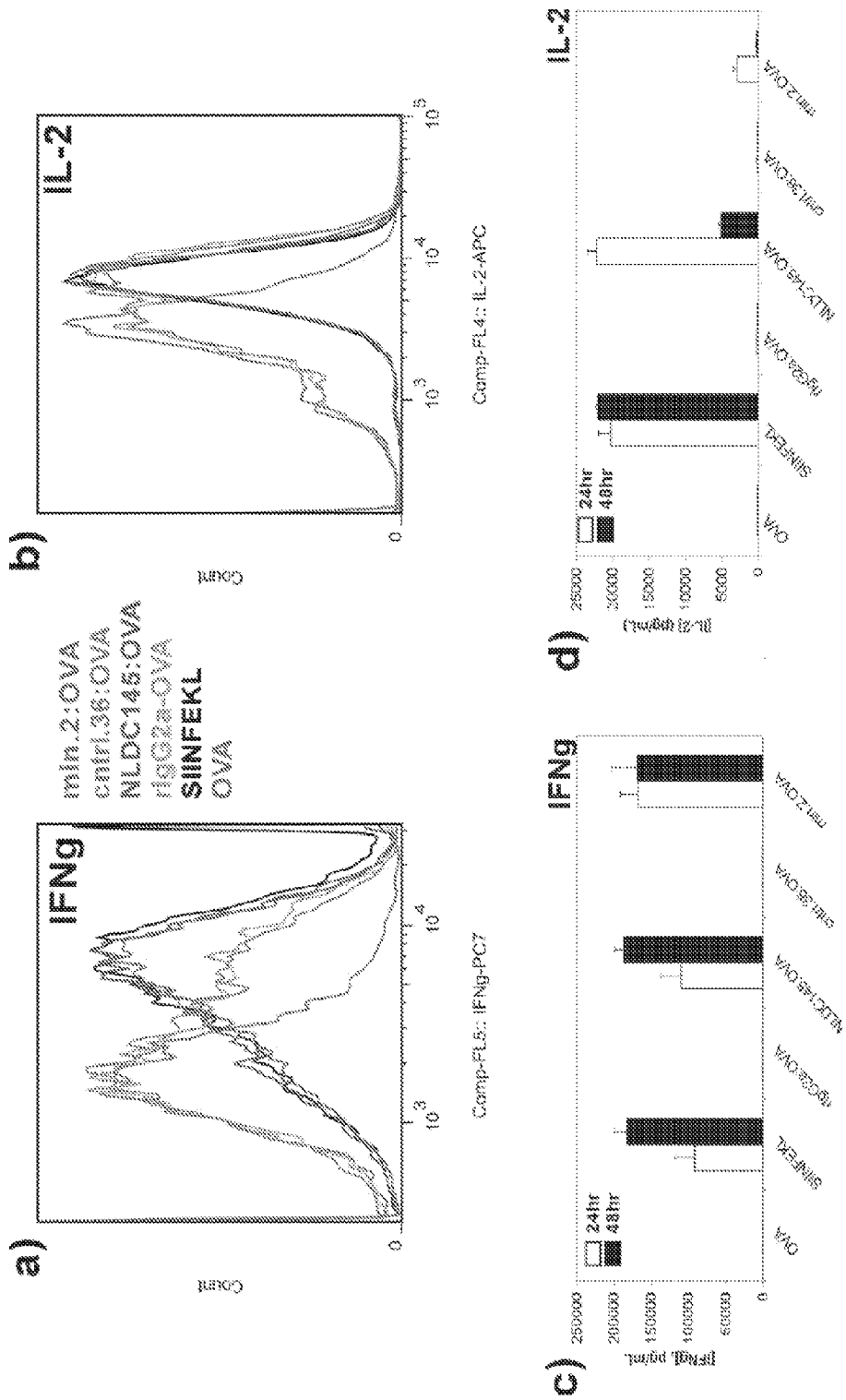
FIG. 6A-6D: OT-I cytokine production. (A, B) Day 2 intracellular cytokine staining. OT-I cells were incubated for two days with 10 nM antigen-treated CD11c+ splenocytes from C57BL/6 mice and analyzed by intracellular flow cytometry for IFNγ or IL-2. See Methods for full procedure. (C, D) Secreted cytokines IFNγ or IL-2 were measured in media 24 hrs or 48 hrs following addition of OT-I cells to 10 nM antigen-treated CD11c+ splenocytes from C57BL/6 mice. OVA—ovalbumin; ELISA—enzyme-linked immunosorbent assay; IFNg/IFNγ—interferon gamma; IL-2—interleukin 2; NLDC145,rIgG2a:OVA—recombinant fusion of OVA and anti-mDEC205 antibody clone NLDC145 or isotype rat IgG2a antibody; min.2,cntrl.36:OVA—OVA chemically conjugated to min.2 or cntrl.36 RNA; SIINFEKL—OVA257-264 peptide (SEQ ID NO:12).

Interestingly, analysis of secreted cytokine levels by ELISA presented a slightly different picture. Targeted delivery by both NLDC145:OVA chimera and min.2:OVA conjugate induced significant secretion of IFNγ by OT-I cells (FIG. 6c), commensurate with the fully activated state indicated by proliferation (FIG. 5b) and ICFC data (FIG. 6a). In contrast, no induction of IL-2 secretion was observed at this time point following incubation with min.2:OVA (FIG. 6d). OT-I cells responded to SIINFEKL (SEQ ID NO:12) loading or anti-mDEC205 antibody-mediated OVA delivery by secreting significant amounts of IL-2. OVA delivery by nonspecific targeting agents (soluble OVA, Iso:OVA or cntrl36:OVA) did not result in cytokine accumulation above background levels. When IL-2 secretion was measured at an earlier time point (1 day post stimulation), min.2:OVA-induced cytokine secretion was observed, albeit at lower levels than seen with NLDC145: OVA-mediated delivery.

Several aptamers that have been used for the targeted delivery of molecular cargoes have not triggered innate immune responses in vitro (21) or in vivo (22,23), and while the FDA-approved aptamer pegaptanib has shown good a safety profile (24), innate immune stimulation may be an aptamer-specific property (25) that requires testing on a case-by-case basis. However, innate immune stimulation may be triggered by specific aptamers, dependent on properties such as RNA sequence (25). Therefore, testing is required on a case-by-case basis. To ensure that the aptamers, which specifically target a DC receptor and are endocytosed, did not provoke any adverse effect on the cells, DCs treated for 24 hrs were monitored with the aptamer-OVA conjugates for upregulation of the activation markers CD80, CD86, CD40 and MHC II (I-A). Importantly, treatment with the aptamer or control conjugates did not produce any changes in expression level beyond that observed by treatment with DBPS alone. (CD11c$^+$ splenocytes were isolated from C57BL/6 mice implanted with Flt3L-expressing B16 melanoma. After isolation, splenocytes were incubated overnight with 10 nM RNA:OVA conjugates in the absence or presence of LPS and poly(I:C). DPBS, OVA and NLDC145: OVA+LPS and poly(I:C) served as reference treatments. Neither cntrl.36:OVA nor min.2:OVA induced DC activation (as measured by CD80 and CD86 expression) above background (DPBS, OVA) levels. Furthermore, neither cntrl.36: OVA+LPS and poly(I:C) nor min.2:OVA+LPS and poly (I:C) induced DC activation above that seen with NLDC145: OVA+LPS and poly(I:C). As expected, only samples treated with polyinosinic:polycytidylic acid (poly(I:C)) and lipopolysaccharide (LPS) showed activation and upregulation of these receptors. Similarly, when cytokine secretion into the media by these same cells was monitored, INFγ, IL-6, IL-10, IL-12, macrophage chemoattractant protein 1 (MCP-1) and tumor necrosis factor alpha (TNFα) all remained at background levels.

Figures 7A, 7B:
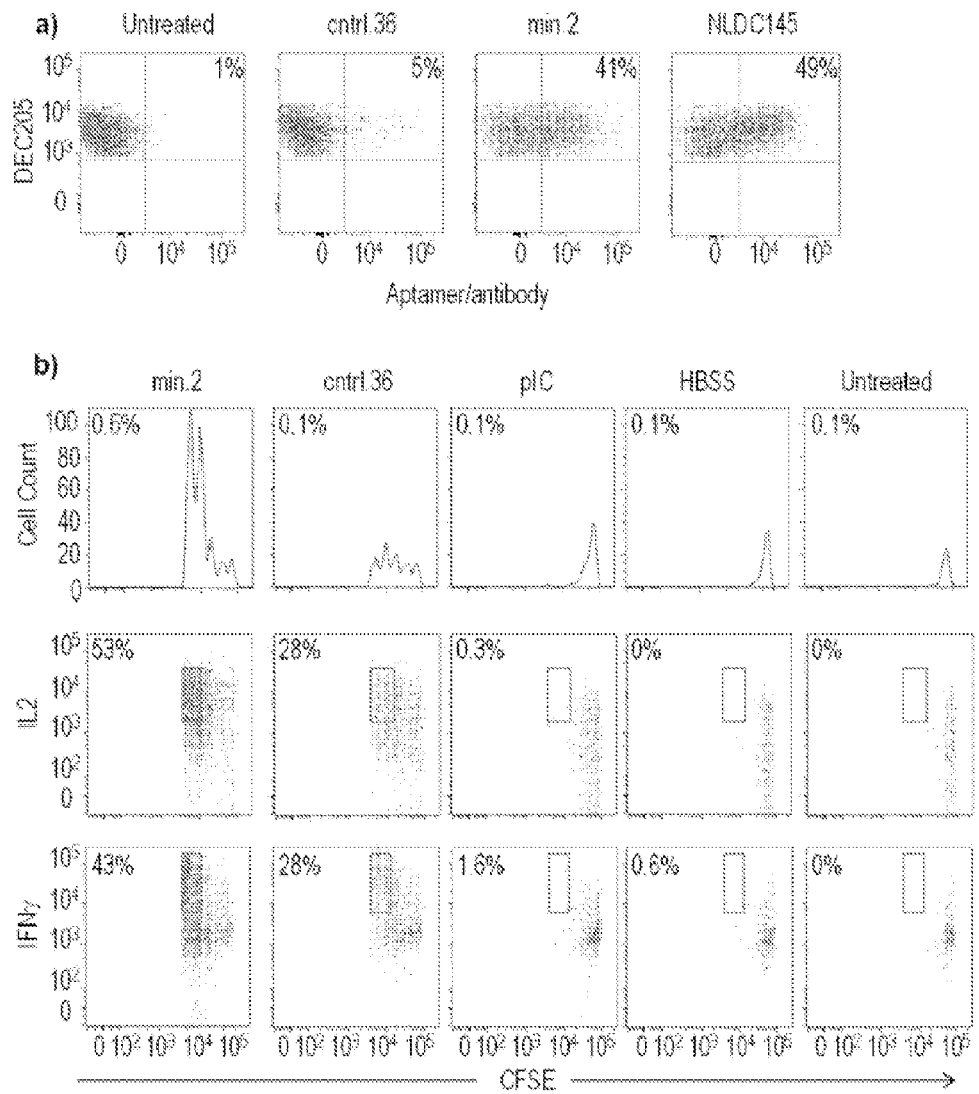
FIG. 7A-7B: Injection of min.2 results in uptake by DEC205+ dendritic cells that is functional for antigen cross-presentation. Mice were injected i.v. with multimerized aptamer that was fluorescently labeled (a) or was conjugated to OVA (b). Uptake by splenic DCs (a) and activation of adoptively transferred OT-I cells (b) was determined. (a) C57BL/6 mice were injected with 20 μg fluorescently labeled multimerized cntrl.36, min.2 or NLDC145 antibody. 24 hours later, spleens were harvested, and aptamer uptake by CD11c+DEC205+ cells was determined by flow cytometry. The percentage of CD11c+DEC205+ cells that have taken up fluorescent aptamer/antibody is reported in each plot. (b) $10^6$ OT-I cells were labeled with CF SE and transferred into congenic B6.SJL-ptprc mice. 24 hours later, mice were injected with 20 μg of aptamer:OVA plus 25 μg pIC. 3 days later, activation status of OT-I T cells was determined by flow cytometry. Proliferation was measured by CFSE dilution (top panel) and IL2 (middle panel) and IFNγ (bottom panel) production determined by intracellular cytokine staining. The number of OT-I cells present, given as a percentage of the total spleen (top panel: % CD45.2+ TCRb+), or the percentage of OT-I cells that have undergone 3 or more divisions and are producing IL2 (middle panel) and IFNγ (bottom panel) is reported within each dot plot. Data shown are representative of three experiments.

Min.2:OVA is functional for cross-presentation in vivo: The ability of min.2:OVA to enhance cross-presentation in vivo was assessed using adoptively transferred OT-I cells. In short, lymph node-derived OT-I cells were labeled with CFSE and injected i.v. into congenic mice (B6.SJL-ptprc). Twenty-four hours later, the mice were injected, i.v., with min.2:OVA or controls. Three days later, spleens were harvested and T cell proliferation and cytokine production was determined by flow cytometry. Consistent with our in vivo targeting results (FIG. 7a), injection of 20 µg min.2: OVA conjugated at a 1:1 ratio failed to elicit T cell proliferation (data not shown). However, when experiments were performed using min.2:OVA conjugates synthesized at a 3:1 aptamer to OVA ratio, significant OT-I proliferation and cytokine production (FIG. 7b) was observed. Injection of min.2:OVA elicited approximately 6-fold more OT-I proliferation when compared with cntrl.36:OVA or other control treatments (OT-I population identified as % CD45.2+ TCRβ+ cells in the spleen; min.2:OVA=0.6%, cntrl.36: OVA=0.1%). Furthermore, cytokine production was highest in animals that received min.2:OVA. In response to min.2: OVA, 53% of splenic OT-I cells that had undergone at least 3 rounds of proliferation produced IL2, IFNγ was detectable in 43% OT-I cells that had divided up to 4 times. In comparison, only injection with ctrl.36:OVA elicited IL2 or IFNγ by OT-I cells (IL2 and IFNγ was detected in 28% of cells that had divided up to 4 times). Other control treatments (pIC alone, HBSS, no injection or OVA alone) did not stimulate responses over background (FIG. 7b and data not shown). Injection with ctrl.36:OVA resulted in some proliferation and cytokine production by OT-I cells. However, the overall level of activation was much less than that observed following min.2:OVA injection. In particular, 6 fold fewer OT-I cells were detected in the spleens of mice given ctrl.36:OVA with these cells producing ~2-fold less IL2 and IFNγ.

Figures 8A, 8B, 8C:
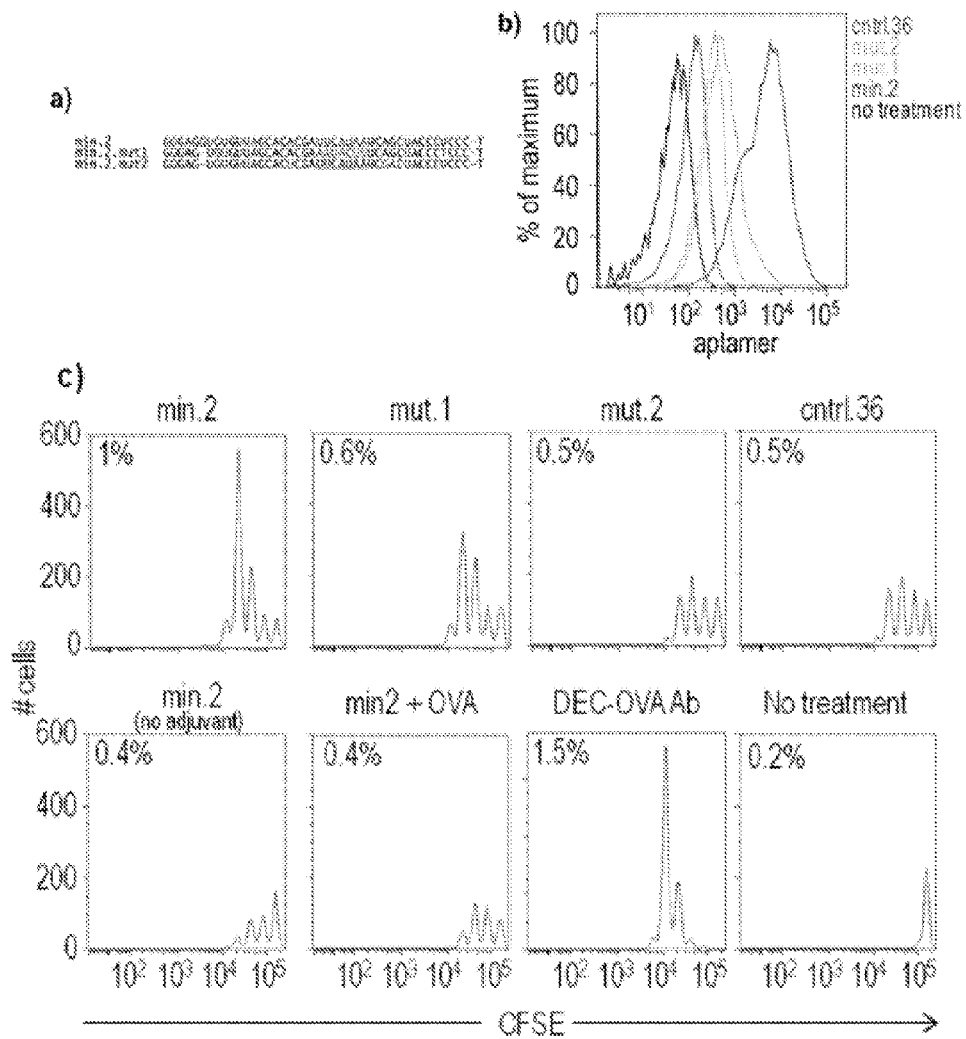

To further confirm that the response observed with min.2: OVA was due to min.2 interacting with DEC205, two mutants of min.2 were generated which largely maintained the sequence composition of the parent aptamer but disrupted the predicted folded structure or the order of nucleotide in the conserved heptamer (FIG. 8a; underlined). To determine binding and uptake of the mutants by DEC205, biotinylated variants or controls were conjugated to AF647-labeled streptavidin at a ratio of 3:1 and incubated with CHO-DEC205 cells. As seen in FIG. 8b, the highest amount of aptamer uptake occurred following incubation with multimerized min.2 (MFI=4647). The multimeric ctrl.36 was taken up 100-fold less efficiently than multimeric min.2 (MFI=39). Although the mutated aptamers were taken up at higher levels when compared with ctrl.36, uptake was significantly reduced compared with min.2: mut.1 uptake was 15-fold lower when compared with min.2 while mut.2 uptake was 9-fold lower (mut.1, MFI=312; mut.2, MFI=500).

Figures 8D, 8E:
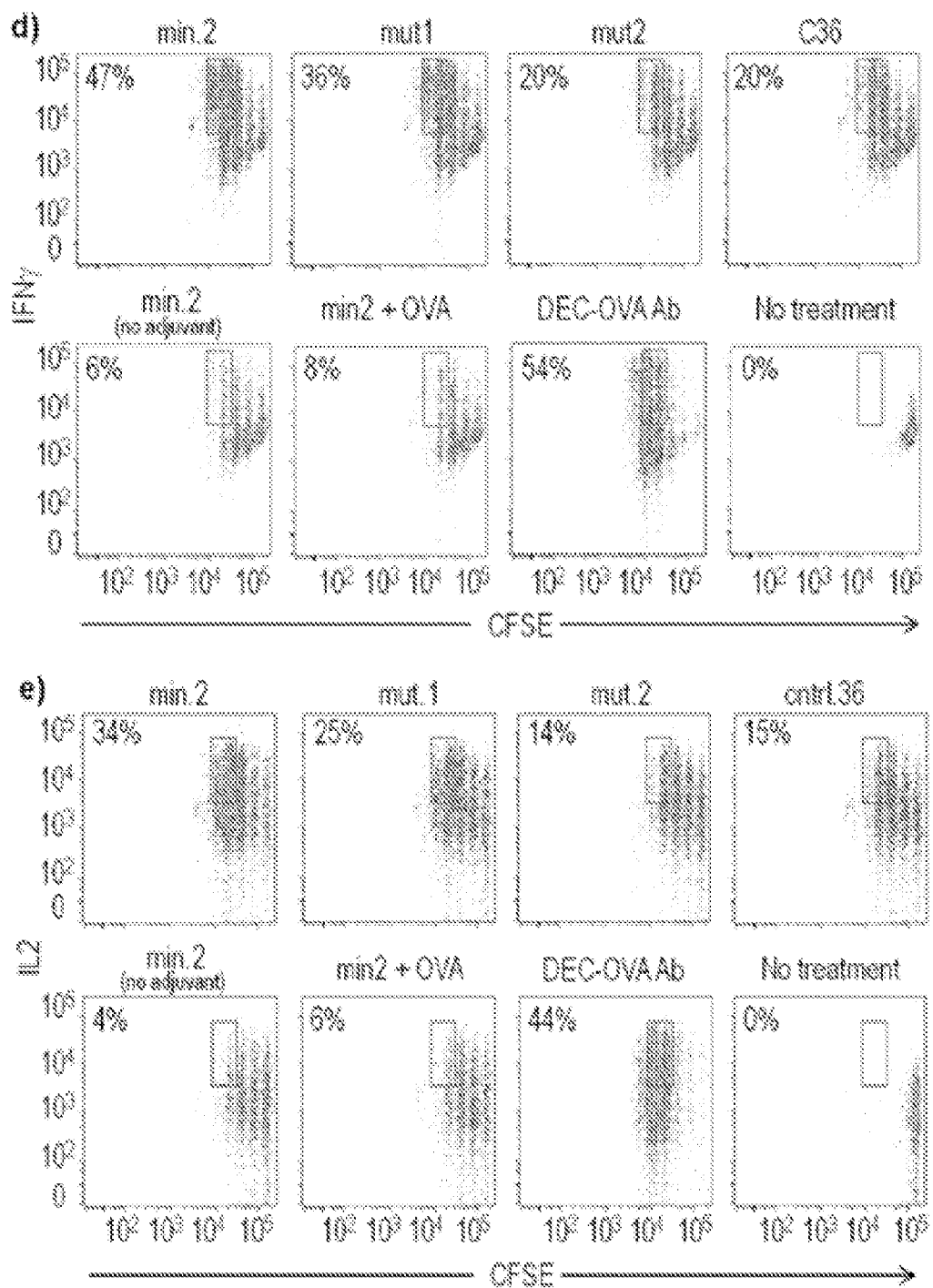

To determine how these mutations would affect T cell activation, the mutated aptamers were conjugated to OVA at a 3:1 ratio and were injected into mice that had received OT-I cells. T cell activation was measured 3 days after aptamer:OVA injection (as in FIG. 7). Injection with min.2: OVA resulted in enhanced OT-I proliferation when compared with various controls, including ctrl.36 and no treatment (FIGS. 8c, 8d and 8e). Additional controls showed that in the absence of the adjuvant pIC, min.2:OVA was not effective in activating OT-I responses (min.2 alone). Furthermore, min.2:OVA is present as a conjugate to elicit activity—when min.2 was admixed with OVA and co-injected (min.2+OVA), minimal OT-I activation was observed. Injection of mut.1:OVA and mut.2:OVA resulted in less activation of OT-I cells compared with min.2:OVA. Injection with mut.1:OVA, mut.2:OVA or ctrl.36:OVA, resulted in similar activation profiles. The percentage of TCRβ+CD45.2+ present (OT-I cells) was 0.5-0.6%, compared with 1% for min.2:OVA and 1.5% for DEC-OVA antibody. When compared to min.2:OVA, cytokine production was slightly diminished following mut.1:OVA injection (IFNγ: 47% vs 36%; IL2: 34% vs 25%). Injection with mut.2:OVA resulted in a greater reduction in responses, with responses observed being similar to those following ctrl.36: OVA injection (IFNγ: 47% vs 20% vs 20%; IL2: 34% vs 14% vs 15%). As expected, treatment with DEC-OVA antibody resulted in high levels of activation, with OT-I cells that had undergone 3 or 4 divisions producing IFNγ (54%) and IL2 (44%).

Discussion

Strategies to specifically target DCs and enhance or control the presentation of antigens by these cells are already finding their way into the clinical trials (16,26). Of particular interest are approaches in which antigens are specifically directed to bind DC cell surface receptors using targeting agents. Receptors such as DEC205, the mannose receptor, CD207, DC-SIGN, Clec9a and DCIR2 and others have been shown to be good molecular targets for directing cargoes to intracellular pathways, which can lead to enhanced antigen presentation (19,26-29). Interestingly, different receptors differ in their ability to stimulate cellular or humoral immunity. This is likely due to factors including cellular expression patterns of the various receptors and to their relative ability to deliver antigenic cargoes to MHC I and II following internalization. For example, in mice, delivery of antigen via the DCIR2 receptor promotes antigen presentation on MHC II, whereas targeting the DEC205 receptor favors MHC I presentation (19). Moreover, co-stimulatory signals can be used to affect downstream T cell responses. For example, co-delivery of adjuvants such as poly(I:C) or anti-CD40 antibodies with antigens conjugated to DEC205-specific antibody leads to DC maturation and the production of sustained $CD8^+$ T cell responses (5,27). However in the absence of such additional signals, the $CD8^+$ proliferation is followed by deletion, leading to tolerance (6). Thus these targeted approaches offer the potential to more finally tune the immunological outcome.

Aptamers that that are specific for surface receptors have previously been used for targeted delivery of molecular cargoes, including small molecule drugs (30), toxins and other proteins (31,32), as well as nanoparticles (33). And while aptamers have been developed to target some immunologically relevant receptors and modulate immune responses (9,34,35), aptamers have yet to be utilized for the targeted delivery of antigens.

To test the potential to utilize aptamers in this capacity, nuclease-stabilized aptamers were generated that targeted mDEC205. Using a minimized variant readily amenable to chemical synthesis, aptamer:OVA conjugates were generated and their ability to specially target $CD11C^+$ $DEC205^+$ DCs and enhance cross-presentation to $CD8\alpha^+$ OT-I T cells in vitro assessed. The anti-mDEC205 aptamer proved efficient at specifically enhancing T cell activation at concentrations as low as 1 nM (FIG. 7b), with no activation observed when similar experiments were performed with a non-targeting oligonucleotide control.

It is interesting to compare the aptamer-targeted results with those of the anti-DEC205 antibody, NLDC145. In the in vitro assays the antibody performed at least 10-fold better than the aptamer showing almost complete activation of the T cell population at 100pM. This fact is perhaps not too surprising considering that the observed binding constant of the aptamer is ~20 nM, and thus appreciable aptamer binding and subsequent uptake would not be expected at concentrations much lower than observed. While the binding affinity of NLDC145 has not been reported, comparable antibodies that target human DEC205 have reported dissociation constants of 100pM-1 nM, 10-100-fold lower than the aptamer (15). A portion of the increased affinity observed with antibodies is a result of their bivalent nature. In the case of the experiments, aptamer-OVA conjugates were generated at a 1:5 aptamer to OVA ratio such that conjugates likely bore only a single aptamer. To the extent that OVA possesses 20 surface lysines, it would be expected that the addition of multiple aptamers could result in enhanced receptor binding and subsequent functional delivery.

It is also interesting to note the differences observed in the production of IFNγ or IL-2 by OT-I cells ~48 hr following exposure of DCs to min.2:OVA conjugate or NLDC145: OVA chimera. IFNγ was detected both intracellularly and in culture supernatants. In contrast, although intracellular IL-2 was observed for both min.2:OVA and NLDC145:OVA, no IL-2 was detected in the culture supernatants for DCs incubated with aptamer-mediated antigen delivery. This apparent discrepancy likely reflects a difference in the magnitude or kinetics of secretion, as IL-2 was detected, albeit at reduced levels, 24 hrs following OT-I incubation with DCs cultured with min.2:OVA. IL-2 is utilized as a T cell growth factor and the lower levels of IL-2 detected in the culture supernatants, when compared with ICFC, coincide with T cell expression of IL-2 receptor (36). While it is known that IL-2 may be dispensable for the initial T cell proliferative response (37), this may have implications for the in vivo testing of aptamer-mediated antigen delivery.

In summary, the work demonstrates a new approach for targeting antigens to specific DC receptors using nucleic acid aptamers. Our anti-mDEC205 aptamers perform well in vitro and demonstrate the ability to target mDEC205+ cells and enhance antigen delivery. Although the aptamer-mediated antigen delivery had a lower efficacy than that observed with the anti-mDEC205 antibody NLDC145, this difference likely rests in differences in the binding affinity of these two targeting agents. To the extent that aptamers have been reported with binding constants in the pM range, it seems likely that future improvements can and will be achieved.

Materials and Methods

Protein expression and purification: Chinese hamster ovary (CHO) cells were cultured in Dulbecco's Modified Eagle Medium (DMEM; GIBCO Invitrogen no. 11995) supplemented with 5-10% fetal bovine serum or 5% Ultra-Low IgG FBS supplemented with antibiotic-antimycotic, and nonessential amino acids (all from GIBCO Invitrogen).

CHO cells, stably expressing an open reading frame for the full-length mouse DEC205 (CHO/mDEC205) were generated as previously described (15). Similarly, the extracellular domain (residues 1-1667) of mDEC205 was fused in-frame with the hIgG1 $F_C$ domain. The mDEC205/hIgG1$F_C$ construct was inserted into the pCMV expression vector (Clontech), transfected into CHO cells to generate stably expressing CHO/mDEC205/hIgG1$F_C$ cells. Culture supernatant from these cells was used to purify the mDEC205/hIgG1$F_C$ fusion protein by affinity to Protein A Sepharose (GE Healthcare).

Aptamer Selection: The sequence of the N50 library used for selection against mDEC205 was: 5' GGGAGGT-GAATGGTTCTACGAT-$N_{50}$-TTACATGCGAGATGAC-CACGTAATTGAATTAAATGCCCGCCATGACCAG-3'. (SEQ ID NO:4) The single stranded DNA library was synthesized such that N regions contained an equal probability of containing A, T, G, or C, as previously described (38). Following deprotection, the library was gel purified by denaturing (7M urea) gel electrophoresis on an 8% polyacrylamide gel. The single stranded DNA library was amplified by PCR to generate a double stranded DNA bearing a T7 promoter and transcribed in vitro using the Y639F mutant of T7 RNA polymerase (39,40) and 2'-fluoro (2'-F) pyrimidines. Following transcription, the RNA was purified on a denaturing (7 M urea) 8% polyacrylamide gel.

For Round 1, ~3 copies of an RNA library encompassing ~$1 \times 10^{14}$ sequences (~20 μg) were utilized. The library, was diluted in 20 μL HBSS (GIBCO) and then thermally equilibrated by incubation at 70° C. for five minutes, followed by room temperature for fifteen minutes prior to addition to the immobilized protein target (mDEC205/hIgG1$F_C$).

Immobilized protein was prepared by incubating 25 pmol mDEC205/hIgG1$F_C$ with 25 μL of washed Dynabeads Protein G resin in 200 uL of washing/blocking buffer (WB, 0.1 M $NaPO_4$ pH 8.2, 0.01% Tween 20). This mixture was incubated 30 minutes at room temperature with rotation and then washed three times with 200 μL DPBS without Ca$^{2+}$ and Mg$^{2+}$ (GIBCO). After the third wash, buffer was removed and replaced with the RNA library. The resin was then incubated for an additional 30 minutes at room temperature with rotation, followed by three washes with 200 μL HBSS. After the third wash, protein and RNA were eluted by a 5 minute incubation with 20 μL 200 mM glycine pH 2.5. The eluant was combined with 400 μL 0.3 M NaOAc, containing 4 μg glycogen and the RNA recovered by ethanol precipitation.

The recovered RNA was reverse transcribed to single-stranded DNA (ssDNA) using Moloney Murine Lukemia Virus reverse transcriptase (M-MLV RT, Invitrogen), the ssDNA was amplified by polymerase chain reaction (PCR) using Taq DNA polymerase, and PCR product was transcribed into 2'-F-Y-RNA by a modified T7 RNA polymerase (Y639F$^{39}$ and P266L$^{41}$ mutations). For subsequent rounds, 1 μg of the previous round's selection product was prepared as above for Round 1.

Prior to Rounds 2 and 3 a negative selection step was used to deplete resin binders of aptamers that bound the F$_C$ region from the population. The negative selection step was performed by incubating the library with 20 μL Dynabeads Protein G resin prepared as above but substituting 50 pmol human IgG1 F$_C$ region (hIgG1F$_C$) for mDEC205/hIgG1F$_C$ fusion protein. Protein G resin loaded with hIgG1F$_C$ was then incubated with the prepared RNA for 30 minutes at room temperature with rotation, after which the resin was spun down and the supernatant was removed and added to 20 μL Dynabeads Protein G resin loaded with 25 pmol mDEC205/hIgG1F$_C$ as above. RNA was recovered, reverse-transcribed, amplified and transcribed as described above.

Round 4 was performed using CHO cells that were stably transfected to express mDEC205. Prior to the positive selection, a negative selection was performed on the parental CHO cells, which no not express this receptor. In short, 5 μg of RNA was combined with a two-fold molar excess of reverse primer used for amplification (T5OR). The mixture was diluted to a final volume of 50 μL in HBSS, denatured 5 minutes at 70° C., and allowed to anneal for 15 minutes at room temperature. Re-annealed RNA was added to ~1×10$^5$ CHO cells in a 24 well plate containing 450 μL and incubated for 30 minutes at 37° C. Following incubation the media (containing non-bound RNA) was removed from the CHO cells and transferred to a well containing ~1×10$^5$ CHO/mDEC205 cells. The RNA was incubated with CHO/mDEC205 for 1 hour at 37° C., after which cells were washed three times with 1 mL HBSS, and cells were lysed for 5 minutes at room temperature with 500 μL TRIzol. Recovered RNA was reverse-transcribed, amplified and transcribed as described above.

For Round 5 an 'internalization selection' was performed in which bone marrow derived dendritic cells (BMDC's) were targeted. BMDC's were prepared from mouse bone marrow by treatment for 5 days with GM-CSF as previously described (17). RNA (5 μg) was combined with a two-fold molar excess of reverse primer used for amplification (T50R). The mixture was diluted to a final volume of 50 μL in HBSS, denatured 5 minutes at 70° C., and allowed to anneal for 15 minutes at room temperature. The RNA was subsequently added to one well of a 24 well plate containing ~5×10$^4$ BMDC's in 450 μL Advanced RPMI 1640 containing 10% FBS and 5% J5 medium (supernatant from B16 melanoma cells transfected to express GM-CSF, courtesy of the Palliser lab) supplemented with single-stranded DNA and transfer RNA (1 mg/mL each).

After a 1 hour incubation at 37° C., the media was removed, and cells were washed three times with 1 mL HBSS containing 0.1% NaN$_3$ followed by a single wash with 1 mL cold 200 mM glycine, 150 mM NaCl, pH 4. The cells were subsequently washed an additional three times with 1 mL HBSS containing 0.1% NaN$_3$ followed by 1 mL DPBS without Ca$^{2+}$ and Mg$^{2+}$ and trypsinized by the addition of 500 μL 0.05% trypsin, 0.53 mM ethylenediaminetetraacetic acid (EDTA) for 15 minutes at 37° C. Following an additional 1mL wash with 1 mL HBSS containing 0.1% NaN$_3$, the cells were pelleted and resuspended in 100 μL with HBSS containing 5 μL RiboShredder ribonuclease cocktail (EpiCentre). The reaction was incubated for 15 minutes at room temperature, after which the cells were washed three times with 1 mL HBSS+0.1% NaN$_3$ and lysed for five minutes at room temperature with 500 μL TRIzol. RNA was recovered, reverse-transcribed, amplified and transcribed as described above.

PCR product from Round 5 was cloned into the pCR2.1-TOPO TA vector by TOPO TA cloning (Invitrogen).

Chemical synthesis of RNA aptamers: Minimized aptamers and controls were synthesized in-lab on an Expedite 8909 DNA synthesizer (Applied Biosystems, Carlsbad, Calif.) using 2'-fluoro-deoxycytidine and 2'-fluoro-deoxyuridine phosphoramidites (Metkinin, Kuusisto, Finland). Unless noted otherwise, all reagents were purchased from Glen Research (Sterling, Va.). The aptamer was synthesized bearing a 5' thiol modification using a thiol-modifier C6 S—S phosphoramidite and a 3' inverted dT residue for added serum stability. The sequences of the minimized aptamer, min.2, and a non-binding aptamer, c36, were: 5S GGGAGGUGUGUUAGCACACGAUUCAUAAUCAGC-UACCCUCCCt (SEQ ID NO:1 with inverted dT) and 5SGGCGUAGUGAUUAUGAAUCGUGUGCUAAUA-CACGCCt (SEQ ID NO:5), respectively, where 't' is a 3'inverted dT and '5S' is the 5' thiol. All aptamers were synthesized with the final 4,4'-dimethoxytrityl (DMT) protecting on left on. Following deprotection, aptamers were purified by reversed phase HLPC on a 10×50 mm Xbridge C18 column (Waters, Milford, Mass.) using a linear gradient of acetonitrile in 0.1M triethylammonium acetate (TEAA) at pH 7.0.

Aptamer Binding by Flow Cytometry: Aptamer binding was assessed by flow cytometery. Rounds from each selection or isolated clones were first hybridized to a biotinylated labeled oligonucleotide that was complementary to the 3' end of the library (TSOR). In a typical assay, 10 pmol of transcribed RNA pool or aptamer was added to 11 pmol biotinylated TSOR (B-TSOR) in 10 μL HBSS or DPBS. The RNA was thermally equilibrated by heating to 70° C. for 3 minutes and then allowed to cool on the bench for 15 minutes at room temperature. The RNA was subsequently added to cells of interest resuspended at 1×10$^5$ cells in 100 μL flow cytometry buffer (HBSS containing 1% BSA and 0.1% NaN$_3$) supplemented with 1 mg/mL ssDNA and/or tRNA. The RNA and cells were incubated for 15 minutes on ice, pelleted by centrifugation and washed once with 1 mL flow cytometry buffer. Cells were resuspended in 100 μL flow cytometry buffer containing 0.5 μL PhycoLink streptavidin-R-phycoerythrin (SA-PE) or PhycoLink streptavidin-allophycocyanin (SA-APC) and incubated an additional 15 minutes on ice, washed with 1 mL flow cytometry buffer, resuspended with 500 μL flow cytometry buffer, and analyzed by flow cytometry, with exclusion of dead cells by 7-aminoactinomycin D (7-AAD) or 4',6-diamidino-2-phenylindole (DAPI) staining.

Flow Cytometry: Fluorophore-conjugated RNA: Thiolated aptamers (5S.min2 or 5S.cntrl36) were used to generate the Alexa Fluor 488 (AF488) aptamers used for flow cytometry. Labeling was performed using AF488-05-malemide (Invitrogen) as follows: thiolated aptamer was reduced using 10 mM tris(2-carboxyethyl)phosphine (TCEP) in 100 µL, of 0.1M TEAA. Samples were heated at 70° C. for 3 minutes followed by incubation at room temperature for 1 hour. The reduced aptamers were desalted using a Biospin 6 column (BioRad, Hercules, Calif.) into PBS supplemented with 50 mM phosphate pH 7.5. To this, AF488-05-maleimide in DMSO was added to a 10-fold molar excess over RNA. Following an overnight reaction at 4° C., the aptamer was desalted an additional time using a Biospin 6 column. In a typical assay, 10 pmol of dye-conjugated RNA was diluted into 10 µL DPBS or HBSS, denatured for 3 minutes at 70° C. and allowed to cool for 15 minutes at room temperature. Cell staining was performed as described above but without the addition of SA-PE or SA-APC.

mDEC205 Knockdown Measurement in CHO/mDEC205: CHO/mDEC205 were transfected in wells of a 12-well plate using Lipofectamine™ 2000 (Invitrogen) and one of two siRNA's directed against mDEC205 (si-mDEC205.1 sense CUAACAACAUGUUGUG-GAAGUGGGT (SEQ ID NO:6) si-mDEC205.1 antisense ACCCACUUCCACAACAUGUUGUUAGUU (SEQ ID NO:7) and si-mDEC205.2 sense GGACUUUGUG-CAUUUGUUAAAGGAC, (SEQ ID NO:8) si-mDEC205.1 antisense GUCCUUUAACAAAUGCACAAAGUCCUU; (SEQ ID NO:9) where underlined residues are DNA), siRNA against the unrelated enhanced green fluorescent protein (EGFP, sense AAGCUGACCCUGAAGUU-CAUCUGCACC, (SEQ ID NO:10) antisense GGUGCA-GAUGAACUUCAGGGUCAGCUU) (SEQ ID NO:11), or a mock (no siRNA) transfection, according to the manufacturer's protocol. Two days after transfection, cells were washed with DPBS without $Ca^{2+}$ and $Mg^{2+}$, lifted from the plate with 5 mM EDTA in DPBS without $Ca^{2+}$ and $Mg^{2+}$, washed with flow cytometry buffer, and resuspended in 100 µL. Cells were then stained with Clone 1 hybridized to B-T5OR or with biotinylated NLDC145 antibody clone (anti-mDEC205), and processed as described above.

mDEC205 Cell Surface Binding Assay: A20.Kb cells or A20.Kb.mDEC205 cells which are engineered to express higher amounts of mDEC205 were washed with RPMI, resuspended at $1 \times 10^5$ cells in 100 µL RPMI supplemented with 1 mg/mL ssDNA, and stored on ice while Alexa Fluor 488-conjugated min.2 and Alexa Fluor 488-conjugated cntrl.36 were prepared as described previously. After addition of refolded RNA to cells, the RNA-cell mixture was incubated for 15 minutes at 37° C., washed with and resuspended in flow cytometry buffer, and analyzed by flow cytometry. Median Alexa Fluor 488 fluorescence of live (DAPI$^-$) cells was plotted versus min.2 or cntrl.36 concentration using GraphPad Prism, and dissociation constant ($K_D$) was calculated by fitting a one site binding model to the data.

A20.Kb cells and A20.Kb.mDEC205 cells were generated from A20 cells by viral transduction. The cell lines were generated by superinfecting retroviruses made from pMX-Kb and/or pMX-mDEC205 as described previously (42).

Synthesis of Aptamer Ovalbumin Conjugate: Thiolated aptamers (5S.min2 or 5S.cntrl36) were used to generate the aptamer OVA conjugates. Pierce Imject Ovalbumin (OVA) was activated with a ten-fold molar excess of N-[γ-maleimidobutyryloxy]sulfosuccinimide ester (sulfo-GMBS, Pierce) in 1 mM EDTA in DPBS without $Ca^{2+}$ and $Mg^{2+}$ according to the manufacturer's protocol, and excess sulfo-GMBS was removed with a Micro Bio-Spin 6 column.

Thiolated aptamers were reduced using 10 mM TCEP and subsequently desalted using a Bio-Spin 6 column into DPBS without $Ca^{2+}$ and $Mg^{2+}$. The reduced aptamers were incubated with a 5-fold molar excess of sulfo-GMBS-activated OVA. The reaction mixture was incubated 30 minutes at room temperature or overnight at 4° C. and then quenched by incubation with excess L-cysteine or BODIPY FL L-cystine (Invitrogen) that had previously been reduced with TCEP. When the latter was used, the conjugate could be used for flow cytometry staining.

The reaction mixture was desalted to 20 mM Tris, pH 7 with a Micro Bio-Spin 6 column and then purified on a Mini Q™ 4.6/50 PE column (GE Healthcare) equilibrated with the same buffer. After washing out the flowthrough, the NaCl concentration was increased linearly to 0.5 M with a steep gradient and held at that concentration until all unconjugated OVA was eluted. Salt concentration was then increased from 0.5 M to 2.5 M over 20 column volumes (CV), at a flow rate of 1 CV per minute. Elution was tracked by monitoring absorbance at 260 nm. Elution fractions were analyzed by electrophoresis on a 7 M urea, 8% acrylamide gel, which was stained with GelStar nucleic acid stain (Lonza) and then scanned on a Storm 840 imager (GE Healthcare). Fractions were pooled, concentrated using Amicon Ultra 10K centrifugal filtration units (Millipore), and buffer exchanged to DPBS before storage at –20° C.

In vitro Proliferation Assays: A single-cell suspension of splenocytes from C57BL/6 mice aged 6 weeks to 6 months was prepared using 400 U/mL collagenase D (Roche), and CD11c$^+$ were isolated using biotinylated antibody clone N418 and MACS streptavidin microbeads, or MACS CD11c$^+$ microbeads alone, according to the manufacturer's protocol (Miltenyi). CD11c$^+$ splenocytes were plated in a 96-well U-bottom plate at $4 \times 10^5$ in 100 µL Advanced RPMI 1640 (Invitrogen) containing 10% FBS, Pen Strep (Invitrogen), GlutaMAX-I (Invitrogen) and 10 mM HEPES (MP-Bio) (complete culture medium), 1 µg/mL lipopolysaccharides from Escherichia coli O111:B4 (LPS, Sigma), and 10 µg/mL polyinosinic-polycytidylic acid (poly(I:C), Sigma). The cells were incubated for 4 hours at 37° C., after which the media was replaced with media of the same formulation containing additional 1 mg/mL ssDNA and 10 nM of either Imject OVA, rat IgG2a isotype antibody-OVA chimera (Iso:OVA, courtesy of the Palliser lab), NLDC145-OVA chimera (DEC:OVA, courtesy of the Palliser lab), cntrl.36:OVA, or min.2:OVA (several wells received an equivalent volume of DPBS as a negative control). The cells were incubated for an additional 16-20 hours at 37° C.

The next day, a single-cell suspension of lymph node cells was prepared from the axillary, brachial, inguinal, popliteal and mesenteric lymph nodes of 6 week-old to 6 month-old C57BL/6 RAG$^{-/-}$ OT-I$^{+/+}$ (OT-I) mice. The OT-I cells were resuspended in DPBS containing 5% FBS, carboxyfluorescein succinimidyl ester (CFSE) was added to 5 µM, and the cells were incubated for 5 minutes at 37° C. protected from light. The reaction was quenched by adding ten volumes of complete culture medium and incubating for five minutes at room temperature. Cells were washed three times in complete culture medium and resuspended in complete culture medium at $1 \times 10^6$ cells/mL. After their 16-20 hour incubation, the CD11c$^+$ splenocytes were washed carefully three times with DPBS, $1 \times 10^5$ CFSE-labeled OT-I cells were added, and the cells were incubated an additional 2-3 days at 37° C. At the end of this incubation, cells were resuspended, washed with flow cytometry buffer, stained with DAPI and antibodies against CD8α and TCRβ, and analyzed by flow cytometry.

In vitro Cytokine Production: CD11c⁺ splenocytes were prepared as described above and treated in triplicate with 10 nM of either of the following: Imject OVA, SIINFEKL ($OVA_{257-264}$) peptide (SEQ ID NO:12), rIgG2a:OVA, NLDC145:OVA, cntrl.36:OVA, or min.2:OVA. OT-I cells were prepared as described above, except for CFSE staining. After 16-20 hour incubation with antigen at 37° C., the CD11c⁺ splenocytes were washed carefully three times with DPBS, and 1×10⁵ OT-I cells were added. Following incubation at 37° C. for two additional days, media was removed and saved, it was replaced with the same media containing 10 μg/mL brefeldin A (BFA, Invitrogen), and cells were incubated for 5 hours at 37° C. Cells were resuspended, fixed with 4% paraformaldehyde (Sigma-Aldrich) in pH 7 PBS for 10 minutes at 37° C., washed, permeabilized with 0.1% saponin (Sigma) in flow cytometry buffer, stained with antibodies against CD8α, TCRβ, interleukin-2 (IL-2) and interferon γ (IFNγ), and analyzed by flow cytometry. The saved media was analyzed for secreted IL-2 and IFNγ by enzyme-linked immunosorbent assay (ELISA).

REFERENCES

1. Steinman, R. M. & Banchereau, J. Taking dendritic cells into medicine. *Nature* 449, 419-426 (2007).
2. D'Argenio, D. A. & Wilson, C. B. A Decade of Vaccines: Integrating Immunology and Vaccinology for Rational Vaccine Design. *Immunity* 33, 437-440 (2010).
3. Palucka, K., Ueno, H. & Banchereau, J. Recent developments in cancer vaccines. *J Immunol* 186, 1325-1331 (2011).
4. Dillman, R. 0. Cancer immunotherapy. *Cancer Biother Radiopharm* 26, 1-64 (2011).
5. Bonifaz, L. C. et al. In vivo targeting of antigens to maturing dendritic cells via the DEC-205 receptor improves T cell vaccination. *J Exp Med* 199, 815-824 (2004).
6. Bonifaz, L. et al. Efficient targeting of protein antigen to the dendritic cell receptor DEC-205 in the steady state leads to antigen presentation on major histocompatibility complex class I products and peripheral CD8+ T cell tolerance. *J Exp Med* 196, 1627-1638 (2002).
7. Yan, A. C. & Levy, M. Aptamers and aptamer targeted delivery. *RNA Biol* 6, 316-320 (2009).
8. Syed, M. A. & Pervaiz, S. Advances in aptamers. *Oligonucleotides* 20, 215-224 (2010).
9. Dollins, C. M., Nair, S. & Sullenger, B. A. Aptamers in immunotherapy. *Hum Gene Ther* 19, 443-450 (2008).
10. Keefe, A. D., Pai, S. & Ellington, A. Aptamers as therapeutics. *Nat Rev Drug Discov* 9, 537-550 (2010).
11. Inaba, K. et al. Tissue distribution of the DEC-205 protein that is detected by the monoclonal antibody NLDC-145. I. Expression on dendritic cells and other subsets of mouse leukocytes. *Cell Immunol* 163, 148-156 (1995).
12. van Broekhoven, C. L., Parish, C. R., Demangel, C., Britton, W. J. & Altin, J. G. Targeting dendritic cells with antigen-containing liposomes: a highly effective procedure for induction of antitumor immunity and for tumor immunotherapy. *Cancer Res* 64, 4357-4365 (2004).
13. Johnson, T. S. et al. Inhibition of melanoma growth by targeting of antigen to dendritic cells via an anti-DEC-205 single-chain fragment variable molecule. *Clin Cancer Res* 14, 8169-8177 (2008).
14. Bozzacco, L. et al. DEC-205 receptor on dendritic cells mediates presentation of HIV gag protein to CD8+ T cells in a spectrum of human MHC I haplotypes. *Proc Natl Acad Sci USA* 104, 1289-1294 (2007).
15. Cheong, C. et al. Improved cellular and humoral immune responses in vivo following targeting of HIV Gag to dendritic cells within human anti-human DEC205 monoclonal antibody. *Blood* 116, 3828-3838 (2010).
16. Celldex Therapeutics. A Study of CDX-1401 in Patients With Malignancies Known to Express NY-ESO-1. In: ClinicalTrials.gov [Internet]. Bethesda (Md.): National Library of Medicine (US). 2009-[2011 Sep. 20]. Available from: http://clinicaltrials.gov/ct2/show/NCT00948961 NLM Identifier: NCT00948961.
17. Inaba, K. et al. Generation of large numbers of dendritic cells from mouse bone marrow cultures supplemented with granulocyte/macrophage colony-stimulating factor. *J Exp Med* 176, 1693-1702 (1992).
18. Heath, W. R. & Carbone, F. R. Cross-presentation, dendritic cells, tolerance and immunity. *Annu Rev Immunol* 19, 47-64 (2001).
19. Dudziak, D. et al. Differential antigen processing by dendritic cell subsets in vivo. *Science* 315, 107-111 (2007).
20. Yokoyama, W. M. et al. Characterization of a cell surface-expressed disulfide-linked dimer involved in murine T cell activation. *Journal of immunology* 141, 369-376 (1988).
21. Chu, T. C., Twu, K. Y., Ellington, A. D. & Levy, M. Aptamer mediated siRNA delivery. *Nucleic Acids Res* 34, e73 (2006).
22. Dassie, J. P. et al. Systemic administration of optimized aptamer-siRNA chimeras promotes regression of PSMA-expressing tumors. *Nat Biotechnol* 27, 839-849 (2009).
23. Pastor, F., Kolonias, D., McNamara Ii, J. O. & Gilboa, E. Targeting 4-1BB Costimulation to Disseminated Tumor Lesions With Bi-specific Oligonucleotide Aptamers. *Mol Ther*. Forthcoming 2011.
24. Apte, R. S. et al. Pegaptanib 1-year systemic safety results from a safety-pharmacokinetic trial in patients with neovascular age-related macular degeneration. *Ophthalmology* 114, 1702-1712 (2007).
25. Wheeler, L. A. et al. Inhibition of HIV transmission in human cervicovaginal explants and humanized mice using CD4 aptamer-siRNA chimeras. *J Clin Invest* 121, 2401-2412 (2011).
26. Morse, M. A. et al. Phase I Study Utilizing a Novel Antigen-Presenting Cell-Targeted Vaccine with Toll-like Receptor Stimulation to Induce Immunity to Self-antigens in Cancer Patients. *Clin Cancer Res* 17, 4844-4853 (2011).
27. Idoyaga, J. et al. Comparable T helper 1 (Th1) and CD8 T-cell immunity by targeting HIV gag p24 to CD8 dendritic cells within antibodies to Langerin, DEC205, and Clec9A. *Proc Natl Acad Sci USA* 108, 2384-2389 (2011).
28. Cheong, C. et al. Microbial Stimulation Fully Differentiates Monocytes to DC-SIGN/CD209+ Dendritic Cells for Immune T Cell Areas. *Cell* 143, 416-429 (2010).
29. Keler, T., He, L., Ramakrishna, V. & Champion, B. Antibody-targeted vaccines. *Oncogene* 26, 3758-3767 (2007).
30. Huang, Y. F. et al. Molecular assembly of an aptamer-drug conjugate for targeted drug delivery to tumor cells. *ChemBioChem* 10, 862-868 (2009).

31. Chu, T. C. et al. Aptamer:toxin conjugates that specifically target prostate tumor cells. *Cancer Res* 66, 5989-5992 (2006).
32. Mallik, P. K., Nishikawa, K., Millis, A. J. & Shi, H. Commandeering a biological pathway using aptamer-derived molecular adaptors. *Nucleic Acids Res* 38, e93 (2010).
33. Farokhzad, 0. C. et al. Targeted nanoparticle-aptamer bioconjugates for cancer chemotherapy in vivo. *Proc Natl Acad Sci USA* 103, 6315-6320 (2006).
34. Dollins, C. M. et al. Assembling OX40 aptamers on a molecular scaffold to create a receptor-activating aptamer. *Chem Biol* 15, 675-682 (2008).
35. McNamara, J. O. et al. Multivalent 4-1BB binding aptamers costimulate CD8+T cells and inhibit tumor growth in mice. *J Clin Invest* 118, 376-386 (2008).
36. Collins, D. P., Luebering, B. J. & Shaut, D. M. T-lymphocyte functionality assessed by analysis of cytokine receptor expression, intracellular cytokine expression, and femtomolar detection of cytokine secretion by quantitative flow cytometry. *Cytometry* 33, 249-255 (1998).
37. Malek, T. R. & Bayer, A. L. Tolerance, not immunity, crucially depends on IL-2. *Nat Rev Immunol* 4, 665-674 (2004).
38. Hall, B. et al. Design, synthesis, and amplification of DNA pools for in vitro selection. *Curr Protoc Nucleic Acid Chem*, Unit 9.2 (2009).
39. Sousa, R. & Padilla, R. A mutant T7 RNA polymerase as a DNA polymerase. *EMBO J* 14, 4609-4621 (1995).
40. Padilla, R. & Sousa, R. Efficient synthesis of nucleic acids heavily modified with non-canonical ribose 2'-groups using a mutantT7 RNA polymerase (RNAP). *Nucleic Acids Res* 27, 1561-1563 (1999).
41. Guillerez, J., Lopez, P. J., Proux, F., Launay, H. & Dreyfus, M. A mutation in T7 RNA polymerase that facilitates promoter clearance. *Proc Natl Acad Sci USA* 102, 5958-5963 (2005).
42. Park, C. G., Lee, S. Y., Kandala, G. & Choi, Y. A novel gene product that couples TCR signaling to Fas(CD95) expression in activation-induced cell death. *Immunity* 4, 583-591 (1996).

What is claimed is:

1. A composition comprising an oligonucleotide aptamer comprising the sequence set forth in SEQ ID NO:1 conjugated to an antigen.

2. The composition of claim 1, wherein the aptamer comprises an oligoribonucleotide.

3. The composition of claim 1, wherein the aptamer is PEGylated.

4. The composition of claim 1, wherein the aptamer consists of the sequence set forth in SEQ ID NO:1.

5. The composition of claim 1, wherein the aptamer further comprises a 3' inverted dT.

6. The composition of claim 1, further comprising one or more additional oligonucleotide aptamers conjugated to the antigen, wherein the aptamers are directed against a cell-surface target of an antigen-presenting cell.

7. The composition of claim 1, wherein the antigen is a vaccine molecule.

8. The composition of claim 1, wherein the composition further comprises an immunological adjuvant.

9. A method of presenting an antigen to a dendritic cell, comprising contacting the dendritic cell with the composition of claim 1 comprising the antigen.

10. A method of eliciting an immune response in a subject comprising administering to the subject the composition of claim 1 comprising the antigen, in an amount effective to elicit an immune response.

11. The method of claim 10, wherein the antigen-presenting cell is a dendritic cell.

12. The method of claim 10, wherein the antigen is a vaccine molecule.

13. The method of claim 10, wherein the cell-surface target is a DEC-205 receptor molecule.

* * * * *